(12) United States Patent
Buck, Jr. et al.

(10) Patent No.: US 11,318,493 B2
(45) Date of Patent: May 3, 2022

(54) MULTI-REAGENT SLOT DIE COATING PROCESS AND USEFUL DEVICES

(71) Applicant: Roche Diabetes Care, Inc., Indianapolis, IN (US)

(72) Inventors: Harvey B. Buck, Jr., Indianapolis, IN (US); Randall K. Riggles, Indianapolis, IN (US); Thomas D. Hahn, Carmel, IN (US); Mike Limbaugh, Greer, SC (US); Timothy Owens, Pendleton, IN (US)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 21 days.

(21) Appl. No.: 16/604,253

(22) PCT Filed: Apr. 10, 2018

(86) PCT No.: PCT/US2018/026803
§ 371 (c)(1),
(2) Date: Oct. 10, 2019

(87) PCT Pub. No.: WO2018/191207
PCT Pub. Date: Oct. 18, 2018

(65) Prior Publication Data
US 2020/0147638 A1    May 14, 2020

Related U.S. Application Data

(60) Provisional application No. 62/483,696, filed on Apr. 10, 2017.

(51) Int. Cl.
*B05C 5/02* (2006.01)
*B05C 11/10* (2006.01)
(Continued)

(52) U.S. Cl.
CPC .......... *B05C 11/1005* (2013.01); *B05C 5/022* (2013.01); *B05C 5/025* (2013.01);
(Continued)

(58) Field of Classification Search
None
See application file for complete search history.

(56) References Cited

U.S. PATENT DOCUMENTS

| | | | |
|---|---|---|---|
| 3,032,008 A * | 5/1962 | Land | ................ G03C 7/10 118/411 |
| 3,413,143 A | 12/1968 | Cameron et al. | |

(Continued)

FOREIGN PATENT DOCUMENTS

JP    11226469 A  *  8/1999  ........... B05C 5/0254

OTHER PUBLICATIONS

English translation for JP-11226469.*

*Primary Examiner* — Charles Capozzi
(74) *Attorney, Agent, or Firm* — Woodard, Emhardt, Henry, Reeves & Wagner, LLP

(57) ABSTRACT

A slot die shim for use with a slot die, the slot die shim including a first channel configured to receive a first coating, a second channel configured to receive a second coating, and a third channel configured to receive a third coating. The slot die shim simultaneously dispenses the first coating through the first channel, the second coating through the second channel, and the third coating through the third channel onto a substrate. The coatings can be applied at different flow rates and include different test reagents. A vacuum force is applied to the first, second, and third coatings to control a width and a thickness of each of the coatings and a gap or distance between the coatings. The first, second, and third (Continued)

coatings are placed near one another or directly in contact with one another to minimize the area required for the coatings.

9 Claims, 18 Drawing Sheets

(51) Int. Cl.
| | |
|---|---|
| *B05C 9/06* | (2006.01) |
| *B05D 1/26* | (2006.01) |
| *B05D 1/34* | (2006.01) |
| *G01N 27/327* | (2006.01) |
| *B05D 3/04* | (2006.01) |
| *C12Q 1/00* | (2006.01) |

(52) U.S. Cl.
CPC .......... *B05C 5/0254* (2013.01); *B05C 5/0279* (2013.01); *B05C 9/06* (2013.01); *B05D 1/26* (2013.01); *B05D 1/34* (2013.01); *B05D 3/0493* (2013.01); *C12Q 1/005* (2013.01); *C12Q 1/006* (2013.01); *G01N 27/3272* (2013.01); *B05D 2252/02* (2013.01)

(56) References Cited

U.S. PATENT DOCUMENTS

| | | |
|---|---|---|
| 6,159,544 A | 12/2000 | Liu et al. |
| 6,689,411 B2 | 2/2004 | Dick et al. |
| 7,097,673 B2 | 8/2006 | Dudley et al. |
| 7,727,467 B2 | 6/2010 | Burke et al. |
| 7,879,618 B2 | 2/2011 | Mosoiu et al. |
| 7,892,849 B2 | 2/2011 | Burke et al. |
| 8,771,793 B2 | 7/2014 | Wilsey et al. |
| 2003/0097981 A1 | 5/2003 | Dick et al. |
| 2006/0060135 A1 | 3/2006 | Rankin, Jr. et al. |
| 2009/0057944 A1* | 3/2009 | Fork ................ B41J 2/005 264/177.1 |
| 2012/0027942 A1 | 2/2012 | Joos |
| 2012/0032157 A1* | 2/2012 | Kawabe ........... H01L 51/0004 257/40 |
| 2012/0111975 A1* | 5/2012 | Ogasawara ......... B05C 5/025 239/589 |
| 2012/0308755 A1* | 12/2012 | Gorman ............ B29C 48/19 428/43 |
| 2013/0133201 A1 | 5/2013 | Schwartz et al. |
| 2014/0242283 A1 | 8/2014 | Joos |
| 2015/0076004 A1 | 3/2015 | Gerber et al. |
| 2016/0152869 A1* | 6/2016 | Rattray ............ B05D 1/34 428/195.1 |
| 2019/0118449 A1* | 4/2019 | Greenlund ......... B29C 48/345 |

* cited by examiner

*Fig. 11A*
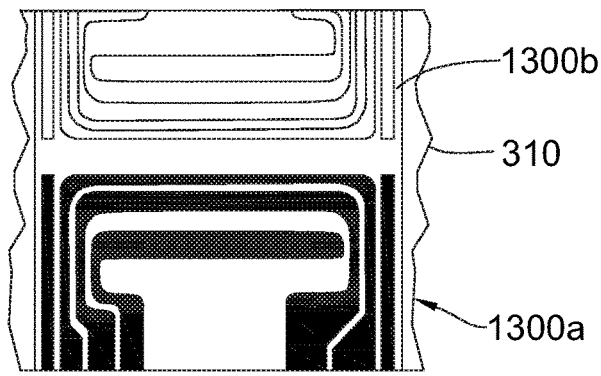
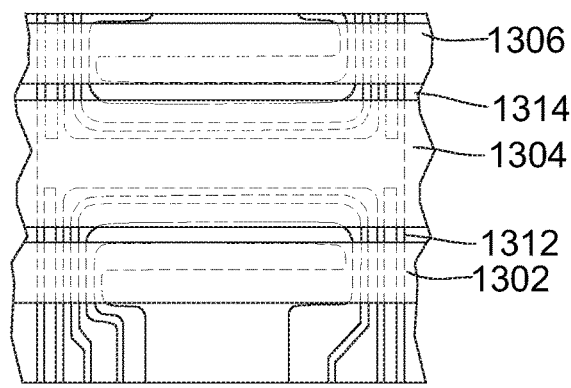
*Fig. 11B*
*Fig. 12A*
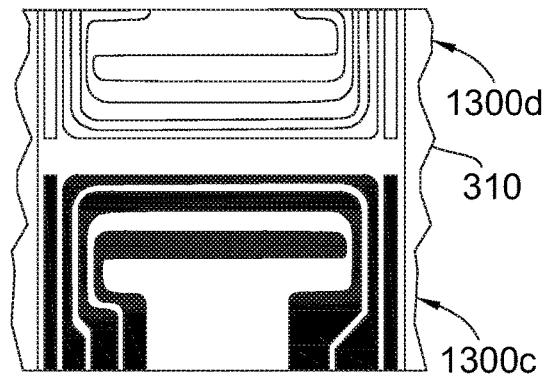
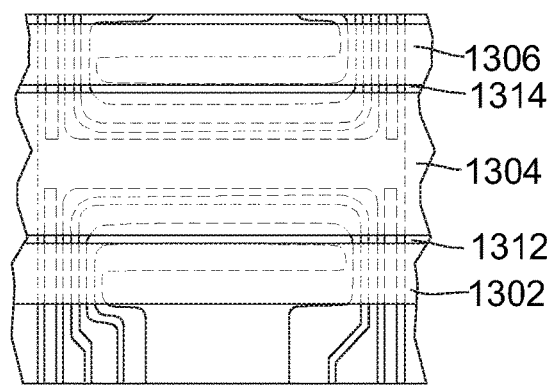
*Fig. 12B*

MULTI-REAGENT SLOT DIE COATING PROCESS AND USEFUL DEVICES

BACKGROUND

To assay multiple analytes on a single test element, or assay a single analyte with multiple reagents on a single test element, reagents are applied to different discrete areas of the test element. One technique of dispensing reagents onto a substrate of the test element includes ink jet application of the reagents. Ink jet application of reagents can create accurate reagent patterns on the substrate; however, the ink jet application is limited by the viscosity of the reagent liquid that can be applied by the ink jet. Typically ink jet application of reagents requires a low viscosity for the reagents for proper placement. As such, ink jet application typically does not apply reagents with a high viscosity. Another difficulty with the ink jet application is controlling the area and the profile of the reagent that is applied to a substrate.

Another technique of dispensing reagents onto a substrate includes slot die coating techniques. A slot die coating head is placed in close proximity to the substrate and dispenses a contiguous reagent film onto the substrate. The reagent film placed with the slot die coating head can cover a wide area on the substrate. However, the slot die coating head does not allow for placement of multiple reagent films within a small area on the substrate. The slot die coating head can be fabricated by machining channels for multiple reagents directly into the head, but this arrangement would provide limited flexibility and re-use opportunity for alternative configurations of the reagents. Any change in the desired dimensions or separation of the channels in the slot die coating head would require remanufacture of the entire slot die coating head which is costly and time consuming.

In an alternative technique, the slot die coating head can include a thin shim placed therein. The shim can include openings for reagents to flow onto the substrate when the slot die coating head is placed in close proximity to the substrate. One shortcoming to the thin shim having two openings is that the openings must be positioned relatively far apart for the shim to have the required structural integrity and strength for the portion of the shim between the openings. With the openings being placed relatively far apart, the corresponding reagent films are also placed far apart on the substrate. A wider distance between the reagent films can also require a larger bodily fluid sample size to cover the two reagent areas. The openings in the shim also dispense and form a thicker layer of reagent on the substrate that can therefore require a larger bodily fluid sample size to wet the reagent layer. Thicker reagent layers with a large gap distance between the layers can lead to spreading and mixing of the reagent layers, which may affect any test results. Moreover, it is even more problematic to include more than two openings and maintain the structural integrity of such thin shims, as well as maintain a workable distance among the corresponding reagent films placed on the substrate.

Thus, there is a need for improvement in this field.

SUMMARY

One aspect concerns a method for applying a plurality of wet films to a substrate, comprising providing a slot die having a slot die shim positioned near a discharge end of the slot die, the slot die shim having a plurality of channels, applying a plurality of coatings through the plurality of channels, and dispensing the plurality of coatings simultaneously onto the substrate.

Aspect 2 concerns the method of aspect 1, further comprising applying a vacuum force adjacent the discharge end of the slot die.

Aspect 3 concerns the method of aspect 2, wherein the vacuum force creates a pressure differential between an upstream side of said discharge end and a downstream side of said discharge end, and wherein said pressure differential is between about 10 Pa and about 800 Pa.

Aspect 4 concerns the method of any one of aspects 2-3, further comprising adjusting the vacuum force in real-time while applying the plurality of coatings to control a width and a thickness of each of the plurality of coatings.

Aspect 5 concerns the method of any one of aspects 1-4, wherein the substrate includes a plurality of sets of measuring electrodes positioned thereon, and applying the plurality of coatings through the plurality of channels includes forming the plurality of wet films on the plurality of sets of measuring electrodes.

Aspect 6 concerns the method of aspect 5, wherein each set of measuring electrodes includes a combined counter/reference electrode and a working electrode, and the forming the plurality of wet films includes forming a first wet film on the combined counter/reference electrode and a second wet film on the working electrode.

Aspect 7 concerns the method of aspects 4-5, further comprising separating the substrate into a first test element and a second test element.

Aspect 8 concerns the method of any one of aspects 5-7, wherein the plurality of coatings includes a first coating and a second coating, the first coating includes the first reagent for producing a first electrochemical signal in the presence of a first test analyte, and the second coating includes a second reagent for producing a second electrochemical signal in the presence of a second test analyte.

Aspect 9 concerns the method of aspect 8, wherein the first test analyte is glucose and the second test analyte is ketones.

Aspect 10 concerns the method of any one of aspects 8-9, wherein the plurality of coatings includes a third coating, and the third coating includes a third reagent for producing a third electrochemical signal in the presence of a third test analyte.

Aspect 11 concerns the method of aspect 10, further comprising separating the substrate into a first test element and a second test element, the first test element includes the first coating and a portion of the second coating, and the second test element includes the third coating and a remaining portion of the second coating.

Aspect 12 concerns the method of any one of aspects 7-11, wherein the first coating is dispensed in a parallel arrangement with the second coating.

Aspect 13 concerns the method of any one of aspects 1-12, further comprising applying a first coating of the plurality of coatings at a first flow rate through a first flow channel of the flow channels, and applying a second coating of the plurality of coatings at a second flow rate through a second flow channel of the flow channels.

Aspect 14 concerns an apparatus comprising a slot die shim for use with a slot die, the slot die shim having a first channel configured to receive a first coating and a second channel configured to receive a second coating, the slot die shim configured to simultaneously dispense the first coating through the first channel and the second coating through the second channel onto a substrate.

Aspect 15 concerns the apparatus of aspect 14, wherein the slot die shim has a divider wall positioned between the first channel and the second channel.

Aspect 16 concerns the apparatus of aspect 15, wherein the divider wall has a thickness of between about 0.1 millimeters and about 0.5 millimeters.

Aspect 17 concerns the apparatus of any one of aspects 14-16, wherein the first channel has a channel depth of between about 0.1 millimeters and about 0.2 millimeters.

Aspect 18 concerns the apparatus of any one of aspects 14-17, wherein the first channel and the second channel each have a channel width, the channel width of the first channel being smaller than the channel width of the second channel.

Aspect 19 concerns the apparatus of any one of aspects 14-18, wherein the first channel and the second channel each have a dispensing edge, the dispensing edges being arranged in a parallel orientation.

Aspect 20 concerns the apparatus of any one of aspects 14-19, wherein the slot die shim includes a third channel configured to receive a third coating, the slot die shim being configured to simultaneously dispense the third coating through the third channel with the first coating, the second coating, and the third coating arranged parallel to each other on the substrate.

Aspect 21 concerns the apparatus of any one of aspects 14-20, wherein the first coating includes the first reagent for producing a first electrochemical signal in the presence of a first test analyte, the second coating includes a second reagent for producing a second electrochemical signal in the presence of a second test analyte.

Aspect 22 concerns the apparatus of aspect 21, wherein the first test analyte is glucose and the second test analyte is ketone.

Aspect 23 concerns a method for applying the first coating and the second coating to the substrate using the apparatus of aspect 14, the method comprising the steps of applying the first coating having the first reagent for producing a first electrochemical signal in the presence of a first test analyte through the first channel applying the second coating having a second reagent for producing a second electrochemical signal in the presence of a second test analyte through the second channel, and dispensing the first coating and the second coating simultaneously onto the substrate.

Aspect 24 concerns method of aspect 23, further comprising applying a vacuum force adjacent a discharge end of the slot die.

Aspect 25 concerns the method of aspect 24, wherein the vacuum force creates a pressure differential between an upstream side of said discharge end and a downstream side of said discharge end, and wherein said pressure differential is between 10 Pa and about 800 Pa.

Aspect 26 concerns the method of any one of aspects 24-25, further comprising adjusting the vacuum force in real-time while applying the first coating and the second coating to control a width and a thickness of the first coating and to control a width and a thickness of the second coating.

Aspect 27 concerns the method of aspect 26, wherein the controlling includes forming a gap between the width of the first coating and the width of the second coating.

Aspect 28 concerns the method of aspect 26, wherein the controlling includes forming the width of the first coating adjacent to the width of the second coating.

Aspect 29 concerns the method of aspect 28, wherein the width of the first coating is in contact with the width of the second coating.

Aspect 30 concerns the method of any one of aspects 23-29, wherein the substrate includes a plurality of sets of measuring electrodes positioned thereon, and dispensing the first coating and the second coating simultaneously onto the plurality of sets of measuring electrodes.

Aspect 31 concerns the method of aspect 30, further comprising separating the substrate into a first test element and a second test element, the first test element having a first set of the measuring electrodes partially covered by the first coating and the second coating, the second test element having a second set of the measuring electrodes partially covered by the first coating and the second coating.

Aspect 32 concerns the method of any one of aspects 23-31, wherein the first reagent is different from the second reagent.

Aspect 33 concerns the method of any one of aspects 1-13 and 23-32, wherein the reagent has a viscosity of between about 95 to 115 mPa-s and a surface tension of between about 33 and 42 mN/m.

Aspect 34 concerns a method for producing a test element for analysis of one or more analytes in a fluid sample with multiple separate reagents by using the apparatus of aspect 14, wherein the first coating has the first reagent for producing a first electrochemical signal in the presence of a first test analyte, and the second coating has a second reagent for producing a second electrochemical signal in the presence of a second test analyte.

Further forms, objects, features, aspects, benefits, advantages, and embodiments of the present invention will become apparent from a detailed description and drawings provided herewith.

BRIEF DESCRIPTION OF THE DRAWINGS

FIG. 11 is a schematic representation in two steps (A-B) how two electrochemical test elements with three reagent zones having a first gap configuration are manufactured using the slot-die coating process of the present application.

FIG. 12 is a schematic representation in two steps (A-B) how two electrochemical test elements with three reagent zones having a second gap configuration are manufactured using the slot-die coating process of the present application.

DESCRIPTION OF THE SELECTED EMBODIMENTS

Figure 1:
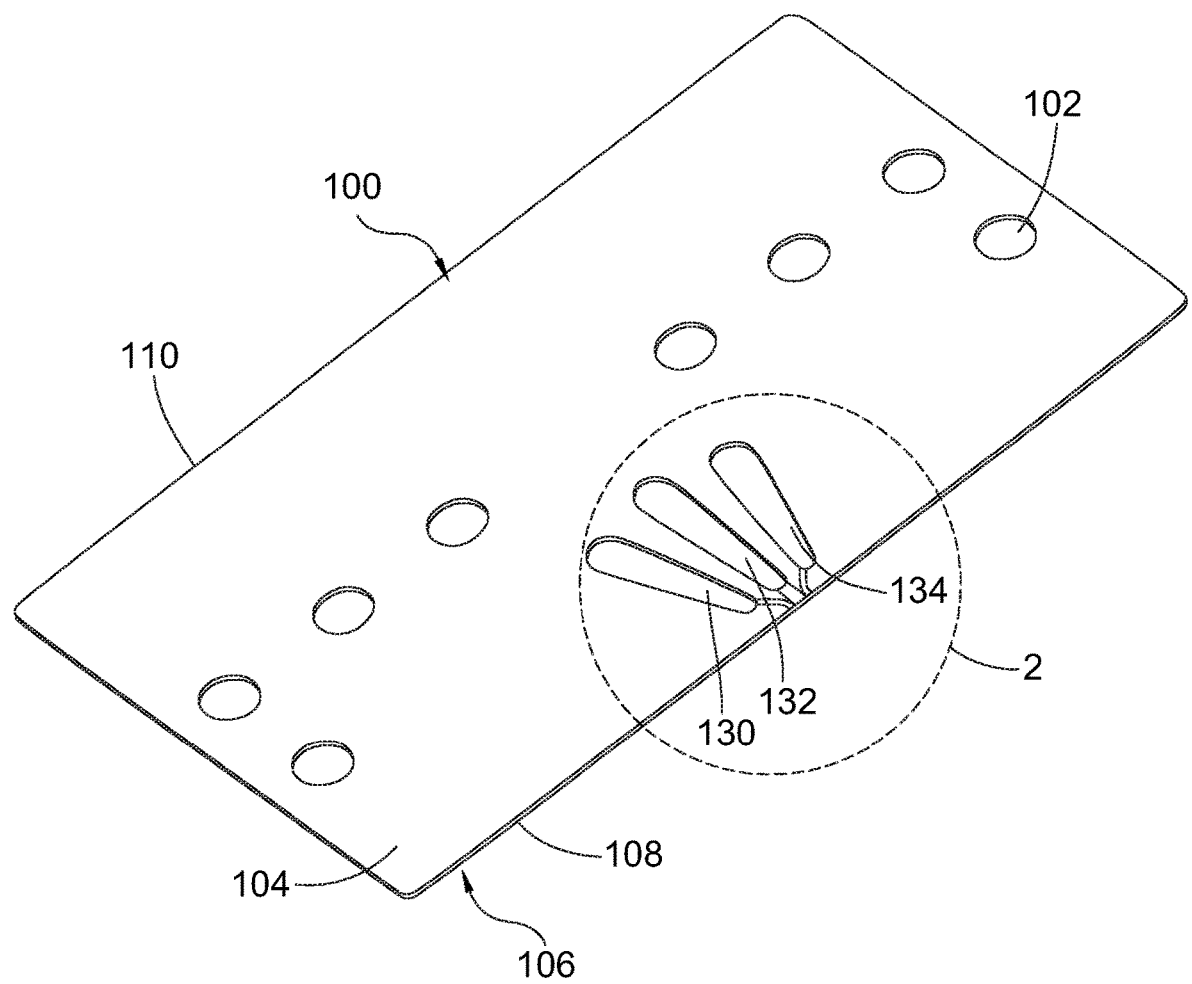
FIG. 1 is a perspective view of a slot die shim according to one embodiment.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

FIG. 1 shows a perspective view of a slot die shim 100. The slot die shim 100 is configured for use with a slot die coating apparatus 300 described in more detail below. The slot die shim 100 includes a plurality of holes 102 that are arranged and configured to enable attachment of the slot die shim 100 to the slot die coating apparatus 300. In particular, the slot die shim 100 is positioned in a slot die assembly 302. The slot die shim 100 is bolted or attached through the plurality of holes 102 when the slot die shim 100 is assembled with the slot die assembly 302. The slot die shim 100 can be attached or assembled with the slot die assembly 302 with other forms or mechanisms of attachment in other embodiments.

The slot die shim 100 has a rectangular configuration in the illustrated embodiment but can be shaped differently in other embodiments. The slot die shim 100 has a thickness T that spans between a top face 104 and a bottom face 106. The slot die shim 100 includes a first channel 120, a second channel 122, and a third channel 124. The slot die shim 100 has a front face 108 opposite a back face 110 wherein the top face 104 and the bottom face 106 span between the front face 108 and the back face 110.

Figure 2A:
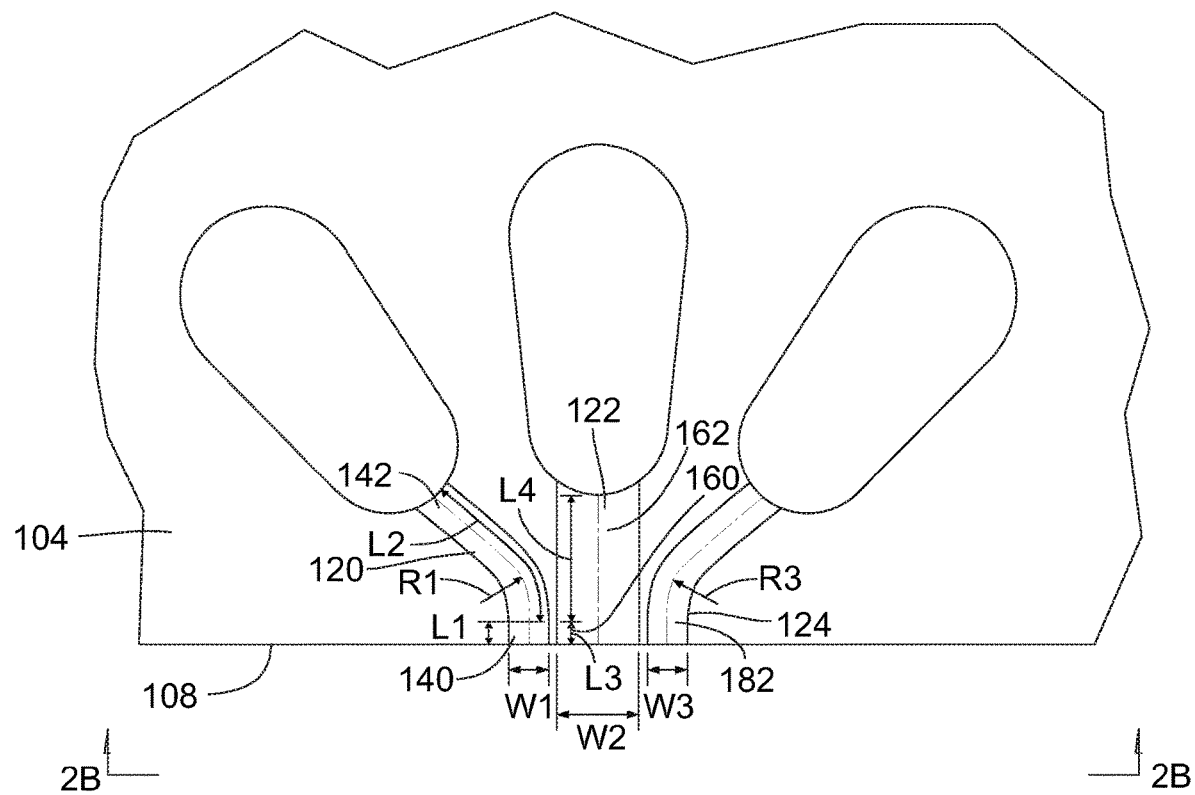
FIG. 2A is an enlarged view of a portion of the FIG. 1 slot die shim as taken along line 2-2 in FIG. 1.

The slot die shim 100 can include any number of channels. In one form, the slot die shim 100 includes only two channels. In another form, the slot die shim 100 includes four or more channels. Additionally, the channels can be arranged to coordinate with the location and orientation of one or more electrodes on substrate material 312 for placement of one or more coatings on the substrate as described in more detail below. In one illustrated embodiment, and as shown in FIG. 2A, the slot die shim 100 includes the first channel 120, the second channel 122, and the third channel 124 that extend through the top face 104 towards the bottom face 106. None of the first channel 120, the second channel 122, or the third channel 124 extends through the bottom face 106. As such, the thickness T of the slot die shim 100 is sufficient for the first channel 120, the second channel 122, and the third channel 124 to be cut or formed therein. There are many techniques in which the first channel 120, the second channel 122, and the third channel 124 are formed in the top face 104. Some of these techniques include cutting, etching, laser cutting, machining, or other techniques in which removal of material from the top face 104 of the slot die shim 100 forms the first channel 120, the second channel 122, and the third channel 124.

The first channel 120 will be described next. The first channel 120 has a first dispensing portion 140 that forms a length L1 of the first channel 120 and a first application portion 142 that forms a length L2 of the first channel 120. Together the length L1 and the length L2 form the total length of the first channel 120. The first dispensing portion 140 and the first application portion 142 can be arranged in any orientation relative to each other that enables fluid connectivity and fluid delivery of the first coating through the first channel 120. For example, the first application portion 142 can be arranged at an angle relative to the first dispensing portion 140 or the first application portion 142 can be aligned with the first dispensing portion 140. As another example, the first application portion 142 can have a radius of curvature and the first dispensing portion 140 can be straight. In one form, the length L1 of the first dispensing portion 140 is between about 0.2 millimeters to about 0.8 millimeters and the first application portion 142 has a radius of curvature R1 of between about 8 millimeters to about 20 millimeters. The first dispensing portion 140 is arranged in a parallel or substantially parallel relationship to a second dispensing portion 160 of the second channel 122 and parallel to a third dispensing portion 182 of the third channel 124. The first dispensing portion 140 includes a first dispensing edge 144 that spans across the width W1 of the first channel 120. In the illustrated embodiment, the first dispensing edge 144 spans across the front face 108. In another form, the first dispensing edge 144 is positioned near the front face 108 to create a step with the front face 108.

Figure 2B:
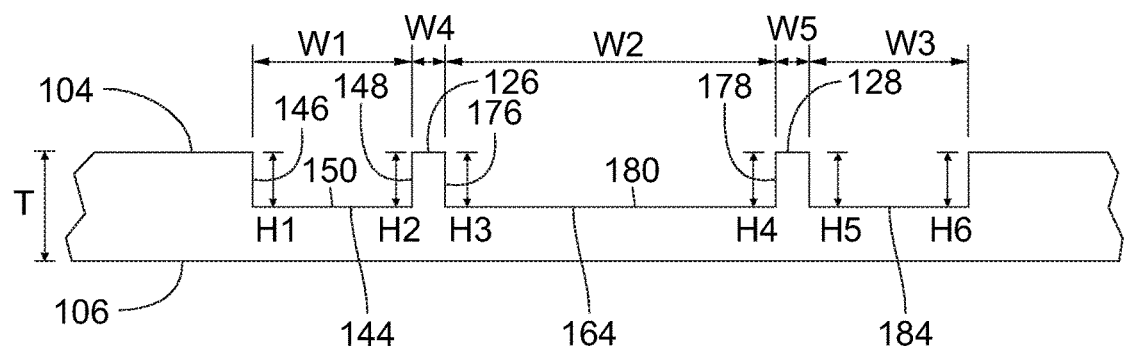
FIG. 2B is a front view of the FIG. 2A portion of the slot die shim.

As shown in FIG. 2B, the first channel 120 includes a first channel wall 146, a second channel wall 148, and a channel floor 150 that span from the first dispensing portion 140 through the first application portion 142 to fluidly connect with the first fluid conduit opening 130. The first channel wall 146 has a height H1 that spans from the channel floor 150 to the top face 104. The second channel wall 148 has a height H2 that spans from the channel floor 150 to the top face 104. The first channel 120 has a channel depth that corresponds to either the height H1 of the first channel wall 146 or the height H2 of the second channel wall 148, whichever is smaller. In one form, the channel depth is between about 0.1 millimeters to about 0.2 millimeters and in one form is 0.127 millimeters. The first channel 120 has a width W1 that spans between the first channel wall 146 and the second channel wall 148 and across the channel floor 150. The width W1 is between about 0.5 millimeters and about 1.0 millimeters. Moreover the width W1 can be constant or vary along the length L1 and the length L2 of the first channel 120. As illustrated, the cross-sectional shape of the first channel 120 is u-shaped. When the first coating is dispensed through the first dispensing portion 140 onto the substrate, the width of the first coating corresponds to the width W1 of the channel floor 150 at the first dispensing edge 144. As discussed in more detail below, the width and thickness of the first coating on the substrate is further controlled or modified by the slot die coating apparatus 300.

The second channel 122 will be described next. As shown in FIG. 2A, the second channel 122 has the second dispensing portion 160 that forms a length L3 of the second channel 122 and a second application portion 162 that forms a length L4 of the second channel 122. Together the length L3 and the length L4 form the total length of the second channel 122. The second dispensing portion 160 and the second application portion 162 can be arranged in any orientation relative to each other that enables fluid connectivity and fluid delivery of the second coating through the second channel 122. FIG. 2A further illustrates the second dispensing portion 160 aligned with the second application portion 162. In one form, the length L3 of the second dispensing portion 160 is between about 0.2 millimeters to about 0.8 millimeters and the length L4 of the second application portion 162 is between about 5 millimeters to about 20 millimeters. FIG. 2B shows that the second dispensing portion 160 includes a second dispensing edge 164 that spans across the width W2 of the second channel 122. In the illustrated embodiment, the second dispensing edge 164 spans across the front face 108. In another form, the second dispensing edge 164 is positioned near the front face 108 to create a step with the front face 108. The second dispensing edge 164 is arranged in a parallel or substantially parallel relationship to the first dispensing edge 144 of the first channel 120 and to a third dispensing edge 184 of the third channel 124.

The second channel 122 includes a first channel wall 176, a second channel wall 178, and a channel floor 180 that span from the second dispensing portion 160 through the second application portion 162 to fluidly connect with the second fluid conduit opening 132. The first channel wall 176 has a height H3 that spans from the channel floor 180 to the top face 104. The second channel wall 178 has a height H4 that spans from the channel floor 180 to the top face 104. The second channel 122 has a channel depth that corresponds to either the height H3 of the first channel wall 176 or the height H4 of the second channel wall 178, whichever is smaller. The channel depth ranges from about 0.1 millimeters to about 0.2 millimeters. The channel depth of the second channel 122 may be the same or different from the channel depth of the first channel 120. The second channel 122 has a width W2 that spans between the first channel wall 176 and the second channel wall 178. In one form, the width W2 is between about 1.0 millimeters and about 2.0 millimeters. In another form, the width W2 is 1.65 millimeters. The width W2 can be constant or vary along the length L3 and the length L4. The width W2 of the second channel 122 is larger than the width W1 of the first channel 120. In one form, the width W2 is about twice as large as the width W1. When the second coating is dispensed through the second dispensing portion 160 onto the substrate, the width of the second coating corresponds to the width W2 of the channel floor 180 at the second dispensing edge 164. As discussed in more detail below, the width and thickness of the second coating on the substrate is further controlled or modified by the slot die coating apparatus 300.

The third channel 124 is similar to the first channel 120 and the second channel 122. In FIG. 2A, the third channel 124 is a mirror image of the first channel 120; therefore, similar details will not be described. In other forms, the third channel 124 can be configured differently.

FIG. 2B shows that the slot die shim 100 also includes a first divider wall 126 positioned between the first channel 120 and the second channel 122. The slot die shim 100 includes a second divider wall 128 positioned between the second channel 122 and the third channel 124. The first divider wall 126 and the second divider wall 128 extend from the top face 104 to the bottom face 106. The first divider wall 126 has a front face width W4 and the second divider wall 128 has a front face width W5 as measured along the front face 108. The width of the first divider wall 126 and the width of the second divider wall 128 increase as the walls 126 and 128 span from the front face 108 towards a first fluid conduit opening 130, a second fluid conduit opening 132, and a third fluid conduit opening 134.

When a first coating is dispensed through the first channel 120 and a second coating is dispensed through the second channel 122, the front face width W4 corresponds to the gap width that is initially provided between the first coating and the second coating. Similarly, when the second coating is dispensed through the second channel 122 and a third coating is dispensed through the third channel 124, the front face width W5 corresponds to the gap width that is initially provided between the second coating and the third coating. In one form, the front face width W4 and front face width W5 are between about 0.1 millimeters to about 0.5 millimeters. As discussed in more detail below, the gap width between the first and the second coatings on the substrate and the gap width between the second and the third coatings on the substrate are further controlled or modified by the slot die coating apparatus 300.

Returning to FIG. 1, the slot die shim 100 includes a first fluid conduit opening 130, a second fluid conduit opening 132, and a third fluid conduit opening 134 wherein the first, second, and third fluid conduit openings 130, 132, and 134, respectively, are sized and configured to respectively receive a first coating into the first channel 120, a second coating into the second channel 122, and a third coating into the third channel 124.

Example dimensions and configurations A1, A2, and A3 for the first channel 120, the second channel 122, the third channel 124, the first divider wall 126, and the second divider wall 128 are provided in the following Table A. These dimensions and configurations are examples only and not intended to limit alternative configurations. All dimensions are measured in millimeters, unless noted otherwise.

TABLE A

| | Channel 120 | | | | | Channel 122 | | | | Channel 124 | | | | | 1st Divider Wall 126 | 2nd Divider Wall 128 | |
|---|---|---|---|---|---|---|---|---|---|---|---|---|---|---|---|---|---|
| | W1 | R1 | L1 | H1 | H2 | W2 | L2 | H3 | H4 | W3 | R3 | L3 | H5 | H6 | W4 | W5 | T |
| A1 | 0.80 | 12.965 | 0.50 | 0.127 | 0.127 | 1.55 | 0.50 | 0.127 | 0.127 | 0.80 | 12.965 | 0.50 | 0.127 | 0.127 | 0.10 | 0.10 | 0.381 |
| A2 | 0.80 | 13.263 | 0.50 | 0.127 | 0.127 | 1.55 | 0.50 | 0.127 | 0.127 | 0.80 | 13.263 | 0.50 | 0.127 | 0.127 | 0.18 | 0.18 | 0.381 |
| A3 | 0.80 | 13.423 | 0.50 | 0.127 | 0.127 | 1.192 | 0.50 | 0.127 | 0.127 | 0.80 | 13.423 | 0.50 | 0.127 | 0.127 | 0.40 | 0.40 | 0.381 |

The slot die shim is configured to simultaneously dispense the first coating through the first channel 120, the second coating through the second channel 122, and the third coating through the third channel 124 onto the substrate by methods, processes, and techniques of the slot die coating apparatus 300 as described next. Other details regarding methods, processes, and techniques of the slot die coating apparatus are found in U.S. Pat. No. 8,771,793 the contents of which is incorporated herein by reference in its entirety.

Figure 3:
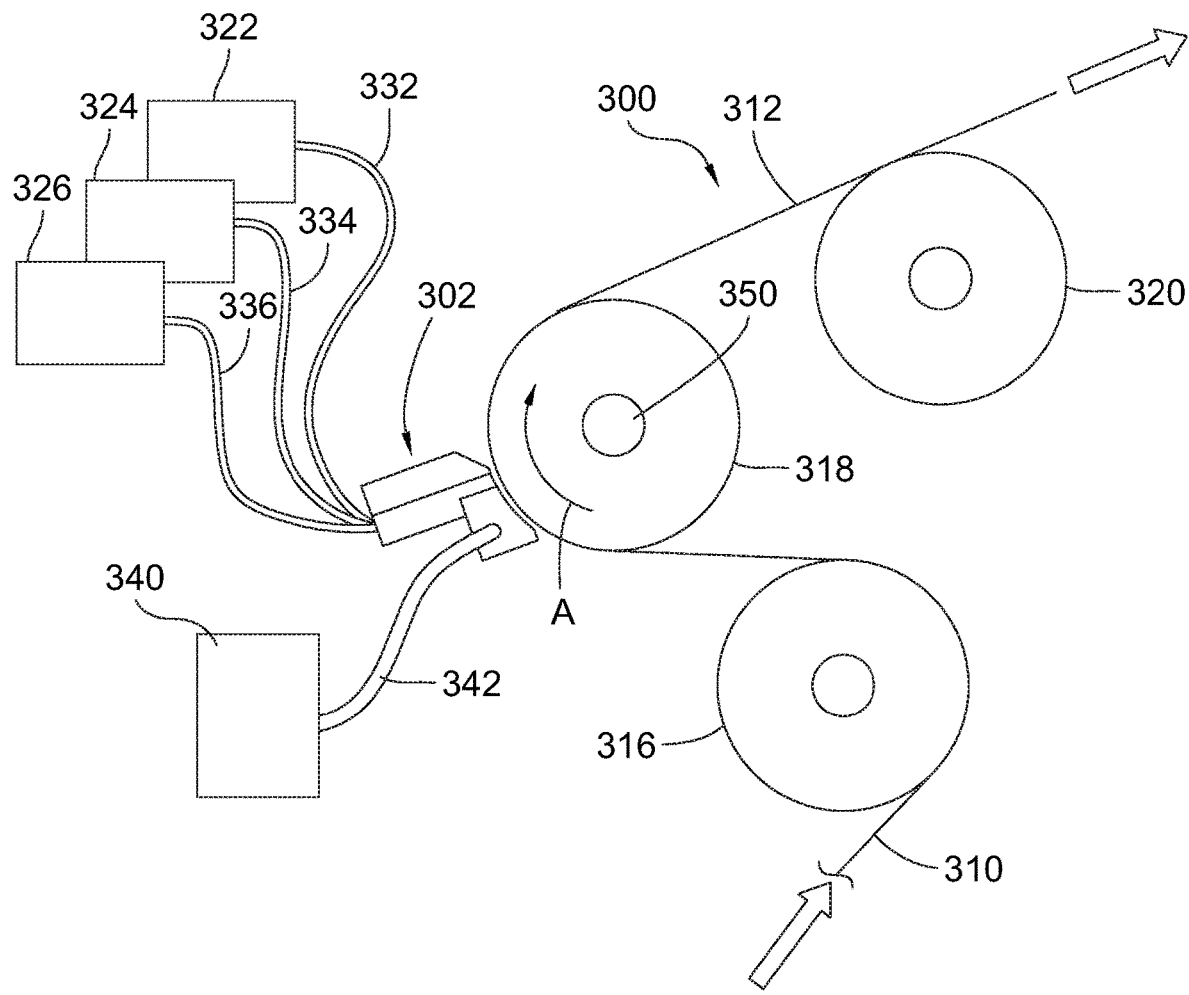
FIG. 3 is a diagrammatic illustration of a slot die coating apparatus.

Referring to FIG. 3, there is illustrated the slot die coating apparatus 300 configured to apply a first coating material (not illustrated), a second coating material 306 (see FIG. 6 for example), and a third coating material (not illustrated) to a web 310 of substrate material 312 from which a plurality of test elements are obtained. The first coating material includes the first reagent for producing a first electrochemical signal in the presence of a first test analyte, the second coating 306 includes a second reagent for producing a second electrochemical signal in the presence of a second test analyte, and the third coating material includes the third reagent for producing a third electrochemical signal in the presence of a third test analyte. The first reagent, second reagent, and the third reagent can be the same reagent or different reagents or any combination of reagents as described in more detail below.

Apparatus 300 includes a first roller 316, a second roller 318, and a third roller 320 through which web 310 is fed. For example, second roller 318 is rotated in a clockwise direction as indicated by arrow A as web 310 is fed through apparatus 300. Apparatus 300 also includes the slot die assembly 302 positioned adjacent to second roller 318, a first reservoir 322, a second reservoir 324, and a third reservoir 326 fluidly coupled with slot die assembly 302 respectively by a first conduit 332, a second conduit 334, and a third conduit 336. The first reservoir 322 is configured to hold a quantity of the first coating material. The second reservoir 324 is configured to hold a quantity of the second coating material 306. The third reservoir 326 is configured to hold a quantity of the third coating material. In some forms, the first reservoir 322, the second reservoir 324, and/or the third reservoir 326 can be fluidly coupled to more than one channel in the slot die shim 100 to supply the same coating material to more than one channel. In one form, in the "EXAMPLES" section of the subject document, the first reservoir 322 is fluidly coupled to both the first channel 120 and the third channel 124 of the slot die shim 100 and the second reservoir 324 is fluidly coupled to the second channel 122. Apparatus 300 also includes a vacuum system 340 coupled with slot die assembly 302 by conduits 342, only one of which is illustrated in FIG. 3. Further details of these features will be provided below in connection with FIGS. 4-8.

Figure 5:
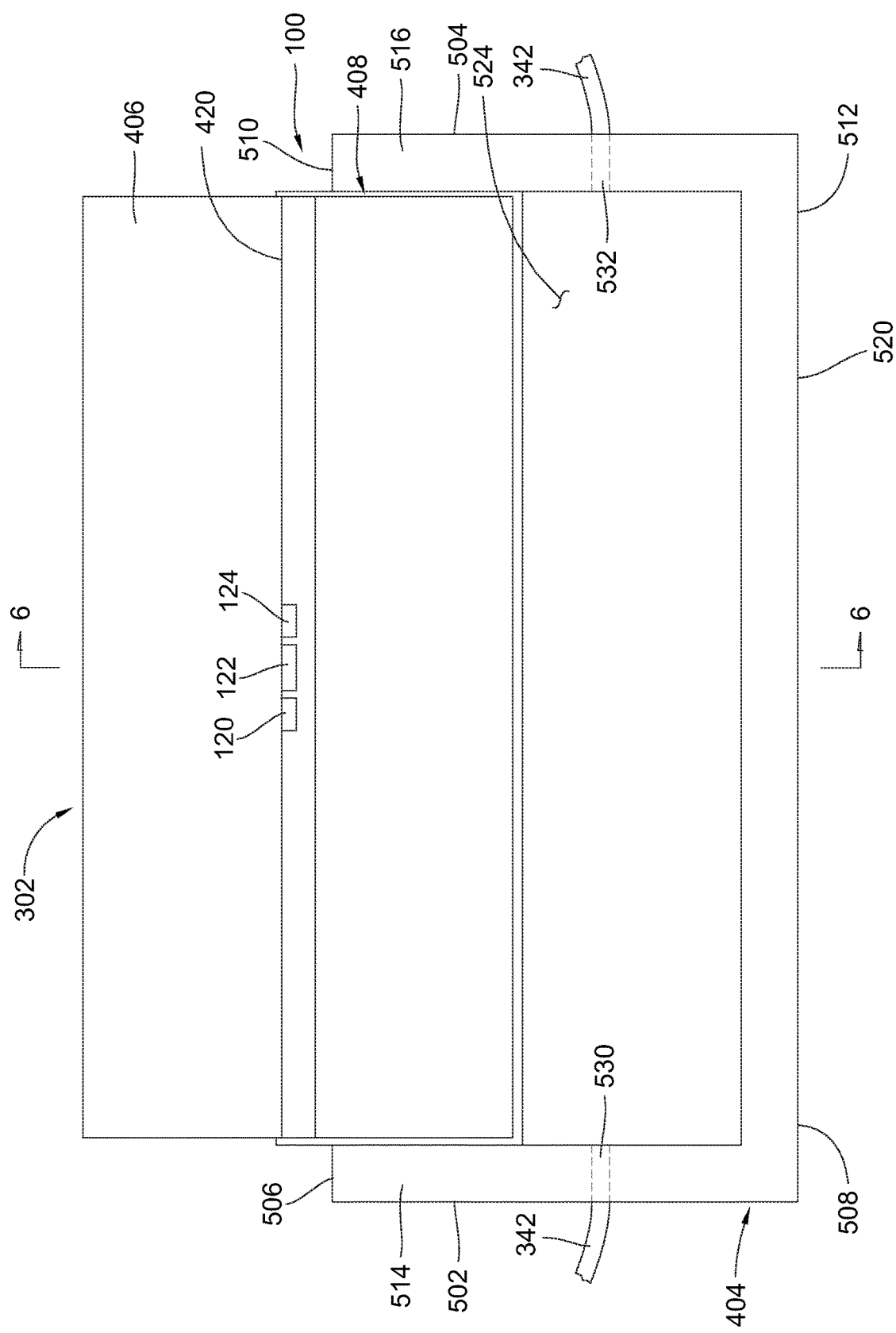
FIG. 5 is a front view of the FIG. 4 slot die assembly with a slot die shim facing the direction of coating flow.
Figure 6:
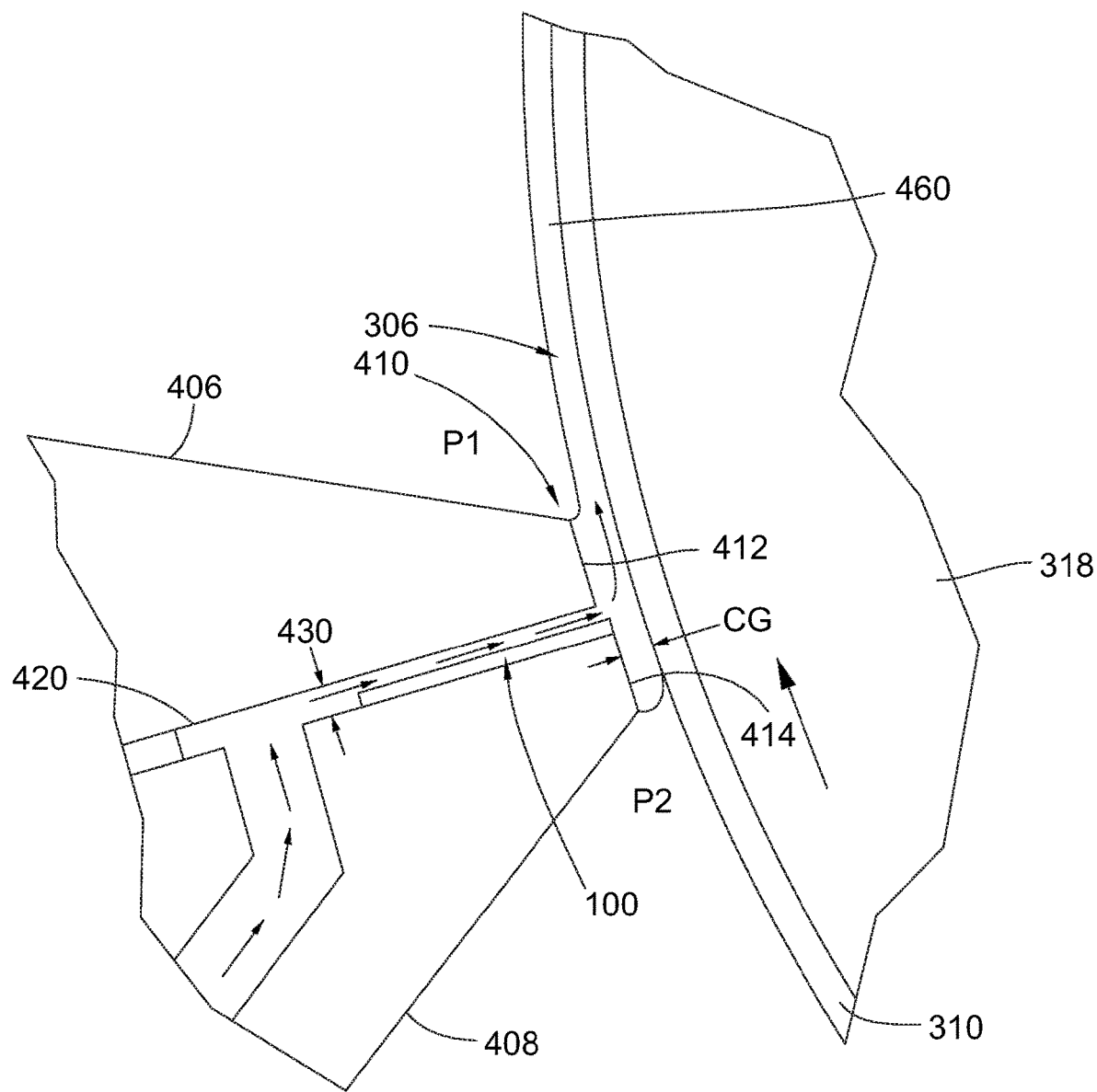
FIG. 6 is a cross-sectional view of the FIG. 5 slot die assembly.
Figure 7:
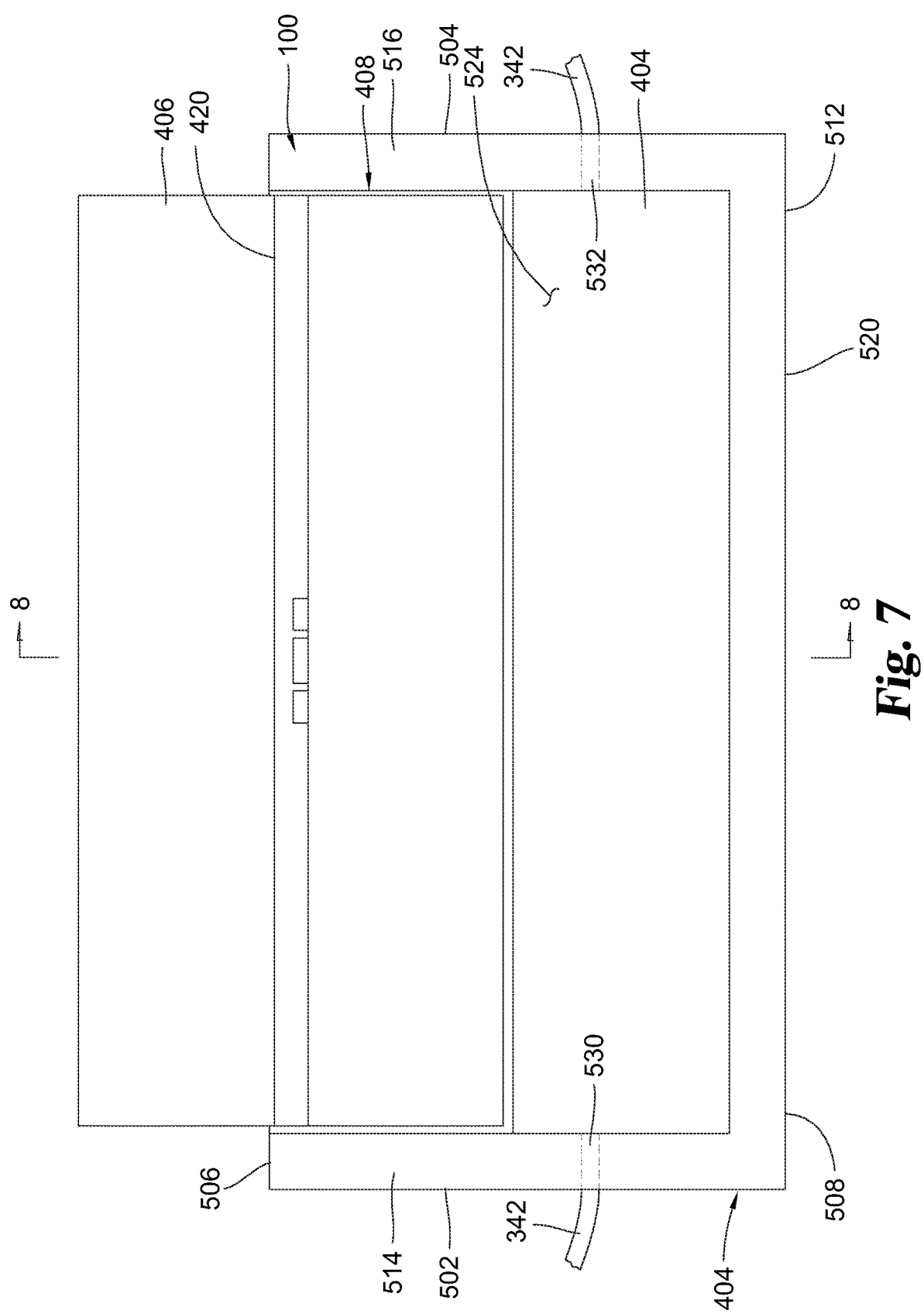
FIG. 7 is the FIG. 5 slot die assembly wherein the slot die shim is positioned in an orientation that is facing away from the direction of coating flow.
Figure 8:
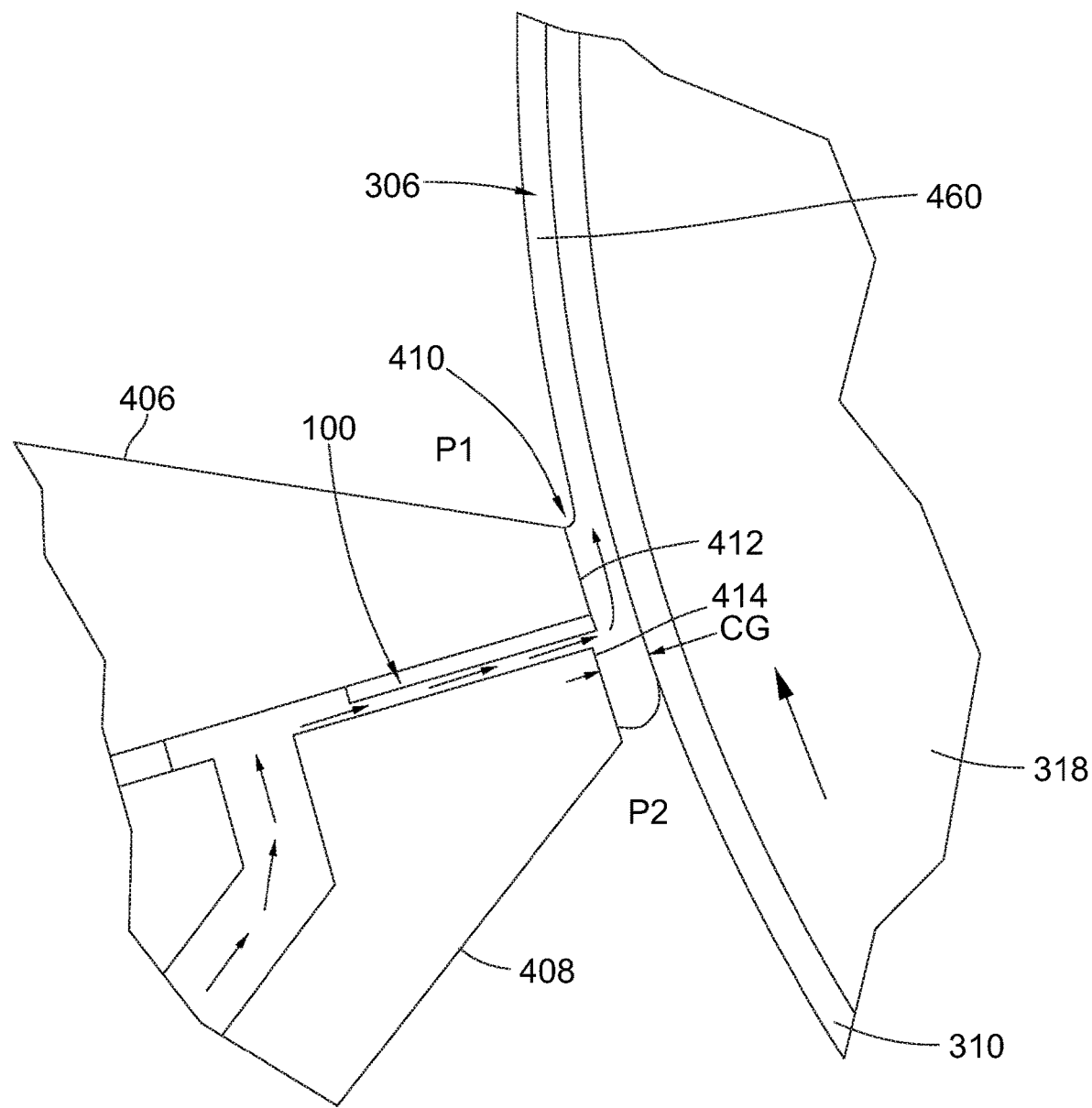
FIG. 8 is a cross-sectional view of the FIG. 7 slot die assembly.

The slot die assembly 302 includes a slot die head 402, the slot die shim 100 attached to the slot die head 402, and a housing 404 that cooperates with slot die head 402 and to which vacuum system 340 is coupled as will be discussed below. Slot die head 402 includes a coating die upper section 406 positioned opposite of a coating die lower section 408. A first arrangement of slot die shim 100 positioned in slot die head 402 illustrated in FIGS. 5 and 6 shows the slot die shim 100 is positioned facing the direction of coating flow. A second arrangement of slot die shim 100 positioned in slot die head 402 illustrated in FIGS. 7 and 8 shows the slot die shim 100 is positioned in an orientation that is facing away from the direction of coating flow. Either configuration of the slot die shim 100 will enable application of the first coating material, the second coating material 306, and the third coating material to the web 310 of substrate material 312. Some considerations in positioning the slot die shim 100 in the slot die head 402 include the direction of flow for the first coating material, the second coating material 306, and the third coating material relative to the direction of travel of the web 310, and the position of the first channel 120, the second channel 122, and the third channel 124 relative to the slot die head 402.

The slot die head 402 includes a discharge end 410 that includes a generally planar surface 412 on coating die upper section 406 facing web 310 and a generally planar surface 414 on coating die lower section 408 facing web 310. In FIG. 6, surface 414 is offset toward web 310 relative to surface 412, and in FIG. 8, surface 412 is offset toward web 310 relative to surface 414, although other forms in which surfaces 412, 414 are even or offset in a different orientation relative toward web 310 are also contemplated. A slot 420 is formed between coating die upper section 406 and coating die lower section 408 and opens through slot die head 402 adjacent to surfaces 412, 414. Slot 420 is sized to receive the slot die shim 100 and either or both of the coating die upper section 406 and/or the coating die lower section 408 can be configured to retain the slot die shim 100 with bolts or other fastening devices through the plurality of holes 102 in the slot die shim 100. In one form (not illustrated), the coating die upper section 406 and the coating die lower section 408 include holes that align with the plurality of holes 102 in the slot die shim 100 for attachment of the slot die shim 100 between both the coating die upper section 406 and the coating die lower section 408. Other forms of attaching the slot die shim 100 with the slot die head 402 can be used. In FIG. 6, the slot die shim 100 is positioned on the coating die lower section 408 such that the front face 108 of the slot die shim 100 is aligned with surface 414. In FIG. 8, the slot die shim 100 is positioned on the coating die lower section 408 such that the front face 108 of the slot die shim 100 is aligned with surface 412. Alternatively, the slot die shim 100 is positioned on the coating die lower section 408 such that at least one of the first dispensing edge 144, the second dispensing edge 164, and the third dispensing edge 184 is substantially aligned with one of the surfaces 412, 414.

Figure 4:
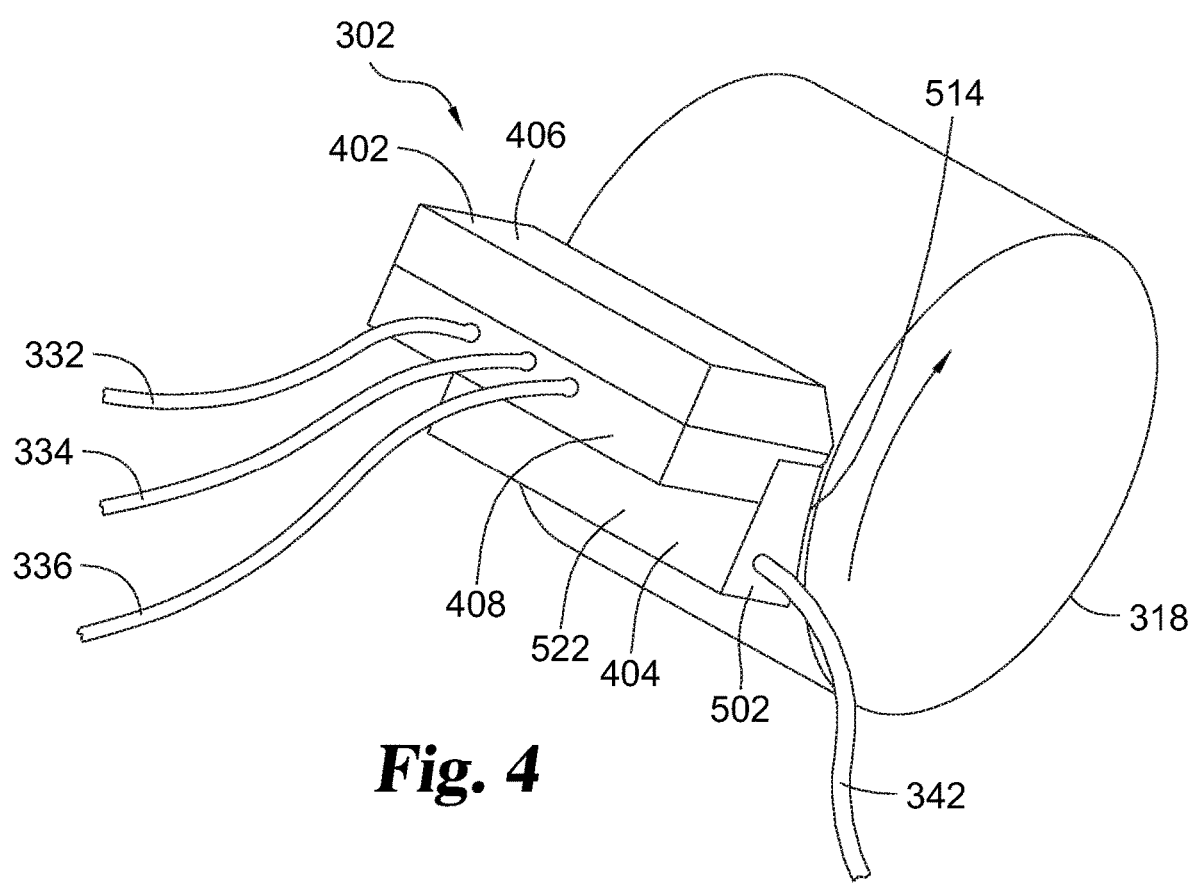
FIG. 4 is an enlarged view of a slot die assembly of the FIG. 3 apparatus.

In the illustrated embodiment in FIG. 4, the first conduit 332, the second conduit 334, and the third conduit 336 are connected to the coating die lower section 408 which is configured to retain and align the conduits 332, 334, and 336 with the first fluid conduit opening 130, the second fluid conduit opening 132, and the third fluid conduit opening 134, respectively, to generally allow the first coating material, the second coating material 306, and the third coating material to be passed through slot die head 402 and the channels 120, 122, and 124 onto web 310, which is positioned between second roller 318 and slot die head 402. In one form, coating die upper section 406 and coating die lower section 408 may be adjustably movable relative to one another to allow changes to the dimensions of slot 420 positioned therebetween and the orientation of the slot die shim 100 relative to the coating die upper section 406 and the coating die lower section 408. Further, in other non-illustrated forms, coating die upper section 406 or coating die lower section 408 may include a drip bib coupled therewith.

Turning now to housing 404, it includes a pair of oppositely positioned lateral side panels 502, 504 (illustrated in FIG. 5), with side panel 502 extending between a first end 506 and a second end 508 and side panel 504 extending between a first end 510 and a second end 512. As illustrated in FIGS. 3 and 4 for example, side panel 502 includes a concavely shaped surface 514 extending between first end 506 and second end 508. In addition, side panel 504 also includes a surface 516 extending between first end 510 and second end 512 that is concavely shaped similar to surface 514. The concavity of surfaces 514, 516 is generally configured to correspond to the convexity of second roller 318 such that side panels 502, 504 can be positioned against or in close proximity to second roller 318. However, in other non-illustrated forms, different configurations for surfaces 514, 516 are contemplated. As illustrated in FIG. 5 for example, a portion of coating die lower section 408 is positioned between side panels 502, 504 and between first ends 506, 510 and second ends 508, 512 thereof. In another example, a portion of the coating die upper section 406 and all of coating die lower section 408 are positioned between side panels 502, 504 and between first ends 506, 510 and second ends 508, 512 thereof such that slot 420 is also positioned between side panels 502, 504 and between first ends 506, 510 and second ends 508, 512. A cross member 520 extends between side panels 502, 504 adjacent second ends 508, 512 on a first side of housing 404 facing second roller 318, and a back panel 522 extends between side panels 502, 504 on an opposite second side. In one or more non-illustrated forms, cross member 520 can include a recessed portion through which web 310 extends as it is moved along second roller 318. Cross member 520 may also include portions on opposite sides of the recessed portion, when present, which can be positioned against or in close proximity to second roller 318.

Side panels 502, 504 and cross member 520 can be positioned in close proximity with second roller 318 such that a generally enclosed environment or chamber 524 is provided upstream from slot 420 and slot die shim 100. Further, as will be explained in greater detail below, surfaces 412, 414 of slot die head 402 and front face 108 of slot die shim 100 are positioned in relatively close proximity to web 310. Similarly, this arrangement of slot die head 402 and slot die shim 100 relative to web 310, as well as the discharge of first coating material from the first channel 120, the second coating material 306 from the second channel 122, and the third coating material from the third channel 124, generally encloses or seals chamber 524 adjacent to first ends 506, 510 of side panels 502, 504 as first coating material, second coating material 306, and third coating material are applied to web 310. It should be appreciated that chamber 524 is generally enclosed or sealed from the surrounding environment when the first coating material, the second coating material 306, and the third coating material are applied to web 310. It should be appreciated that it is not necessary for chamber 524 to be entirely sealed from the surrounding environment, although forms in which it is sealed in such a manner are also contemplated. Rather, it is generally sufficient for chamber 524 to be sealed or enclosed from the surrounding environment in a manner that allows air pressure within chamber 524 to be controlled relative to the surrounding environment, further details of which will be provided below. In one form for example, housing 404 can be positioned relative to second roller 318 such that a gap between about 5 μm and 250 μm extends between second roller 318 and surfaces 514, 516. Forms in which housing 404 is positioned in contact with second roller 318 are also contemplated.

Figure 9:
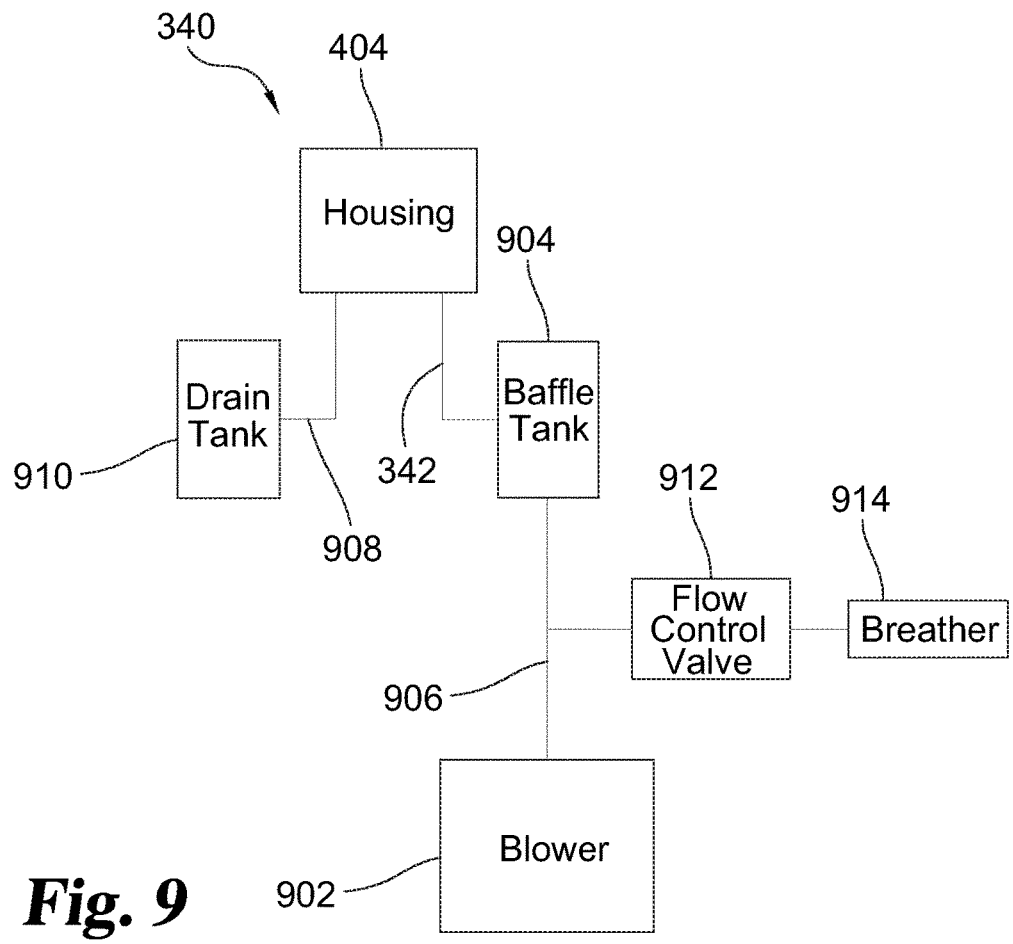
FIG. 9 is a diagrammatic illustration of a vacuum supply system configured to be coupled with the FIG. 4 slot die assembly.

Housing 404 also includes a pair of oppositely positioned outlets 530, 532 which open into chamber 524 opposite of one another and upstream from slot die head 402. In the illustrated form, outlets 530, 532 are coupled by conduits 342 with vacuum system 340 that is operable to regulate air pressure in chamber 524. For example, FIG. 9 illustrates a diagrammatic illustration of one non-limiting form for vacuum system 340 that can be utilized for regulating air pressure in chamber 524. Vacuum system 340 includes a blower 902 that is coupled in fluid communication with a baffle tank 904 by a conduit 906. Blower 902 is generally configured to pull air toward it and away from baffle tank 904 to create a vacuum. In other non-illustrated forms, it is contemplated that the vacuum can be created using a pump or other sources in addition to or in lieu of blower 902. Conduits 342 extend from baffle tank 904 and are coupled with outlets 530, 532 of housing 404. Similarly, the vacuum applied to baffle tank 904 by blower 902 is transferable from baffle tank 904 through conduits 342 to chamber 524. System 340 also includes a conduit 908 that is coupled with and extends between a drain outlet of housing 404 and a drain tank 910 and is operable to drain any liquid that may collect in housing 404.

System 340 further includes a flow control valve 912 that is positioned between blower 902 and baffle tank 904 and in communication with the vacuum force present in conduit 906 when blower 902 is operating. A breather 914 is positioned adjacent to flow control valve 912 and is operable to allow ambient air into conduit 906 in response to certain operations of flow control valve 912. For example, in one form, vacuum system 340 may include one or more sensors configured to determine the strength or level of the vacuum force in conduit 906, baffle tank 904 or chamber 524, just to provide a few non-limiting possibilities, and flow control valve 912 may be responsive to the one or more sensors to adjust the amount of ambient air allowed into conduit 906 to adjust the level of the vacuum force of system 340. In this or other forms, system 340 may also include one or more controllers, such as a frequency inverter driver, configured to control the operation of blower 902 such that the amount or force of the vacuum created by blower 902 is adjusted in response to the vacuum levels measured by the one or more sensors. As indicated above, the illustrated form of vacuum system 340 is non-limiting, and it should be further appreciated that other forms and arrangements are possible and contemplated for system 340.

Referring again to FIG. 6, further details regarding the application of first coating material (not illustrated), second coating material 306, and third coating material (not illustrated) to web 310 to respectively form a first wet film, a second wet film, and a third wet film thereon will now be provided. Similar details from FIG. 6 are applicable to the embodiment illustrated in FIG. 8. It should be appreciated that housing 404 is not illustrated in FIGS. 6 and 8 in order to enhance clarity. The following parameters and description are applicable to the application of first coating material, second coating material 306, and third coating material in the respective form of the first reagent material, a second reagent material 460, and the third reagent material to web 310. Similarly, it should be appreciated that alternative values for the process parameters discussed below may be applicable to the slot die coating technique described herein for use with other forms of first coating material, second coating material 306, and third coating material or upon the occurrence of other changes. In addition, it should also be appreciated that the below-described parameters may also change as the desired thickness T and width W (FIG. 13) of each of a first wet film 602, a second wet film 604, and a third wet film 606 changes from the values described below.

Discharge end 410 of slot die head 402 is positioned in close proximity to web 310 such that a coating gap CG extends there between. In one non-limiting form, coating gap CG is between about 20 μm and about 600 μm. In another more particular form, coating gap CG is between about 40 μm and about 450 μm. Still, in another more particular form, coating gap CG is between about 40 μm and about 200 μm. For example, coating gap CG is 170 μm. However, it should be appreciated that alternative values for coating gap CG are possible and contemplated and can be affected by the rheology and weight of first coating material, second coating material 306, and third coating material, surface tension and speed of web 310, the radius of second roller 318, the lengths of coating die upper section 406 and coating die lower section 408 of slot die head 402, inlet gap and length of slot die head 402, and the angle, if any, of coating die upper section 406 relative to the coating die lower section 408. Alternative values for the coating gap CG are also affected by the configuration of the first channel 120, the second channel 122, the third channel 124, the first divider wall 126, and the second divider wall 128. The depth of the first channel 120, depth of the second channel 122, and depth of the third channel 124 also affect the coating gap CG.

In one form, slot 420 includes a width between side panels 502, 504 for receiving the slot die shim 100 to apply first coating material, second coating material 306, and third coating material through the first channel 120, second channel 122, and the third channel 124. The slot 420 also includes a height 430 between coating die upper section 406 and coating die lower section 408 that corresponds to the thickness T of the slot die shim 100. For example, height 430 is between about 100 μm and about 500 μm. In one particular form, the height 430 of slot 420 is about 381 μm. As illustrated in FIG. 6 for example, slot die head 402 generally extends orthogonally to web 310 at the location where discharge end 410 is positioned adjacent thereto. However, in other forms it is also contemplated that slot die head 402 can extend obliquely relative to web 310. In addition, as best seen in FIG. 3 for example, slot die head 402 is oriented at an oblique angle relative to a central axis 350 of second roller 318 which, in one form, can be between about 10 degrees and about 25 degrees, although other variations are also contemplated.

As indicated above, web 310 is moved relative to slot die assembly 302 by one or more of first roller 316, second roller 318, and third roller 320 of apparatus 300. In one form, web 310 is moved relative to slot die assembly 302 at a rate between about 35.0 m/min and about 45.0 m/min. In another more particular form, web 310 is moved relative to slot die assembly 302 at a rate of about 10.0 m/min. Other variations for the rate at which web 310 is moved are contemplated depending on the desired width and thickness of each of the first coating material, second coating material 306, and third coating material relative to the particular application of the method and apparatus disclosed herein, and also depending on the flow rates of the discharged first coating material, second coating material 306, and third coating material. For example, in certain experimental coating processes described in greater detail below in the "EXAMPLES" section of the subject document, the web was moved relative to the slot die assembly at a rate between about 8.0 m/min and 12.0 m/min, and more particularly at a rate of about 10.0 m/min.

Figure 14:
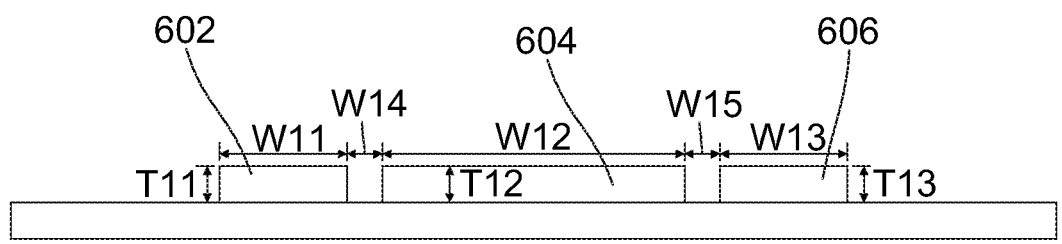
FIG. 14 is a schematic representation of a side view of a substrate material on which a first wet coating film, a second wet coating film, and a third wet coating film have been formed.

As web 310 is moved relative to slot die assembly 302, first coating material, second coating material 306, and third coating material are delivered to slot die head 402 from first reservoir 322, second reservoir 324, and third reservoir 326, respectively, using, by way of non-limiting example, one or more pumps, pistons, syringes, or bladder systems for each of the reservoirs 322, 324, and 326. As another example, multiple positive displacement pumps or other devices can be used with the reservoirs 322, 324, and 326 so that first coating material, second coating material 306, and third coating material can be applied at different flow rates. First coating material, second coating material 306, and third coating material are respectively forced through the first conduit 332, the second conduit 334, and the third conduit 336 and into the slot die head 402. The first conduit 332, the second conduit 334, and the third conduit 336 are respectively connected with the first fluid conduit opening 130, a second fluid conduit opening 132, and a third fluid conduit opening 134 to enable the first coating material, second coating material 306, and third coating material to flow into the first channel 120, the second channel 122, and the third channel 124. The first coating material, second coating material 306, and third coating material exit the first channel 120, the second channel 122, the third channel 124, and the slot 420 at discharge end 410 where it is applied onto web 310 of substrate material 312 to form first wet film 602, second wet film 604, and third wet film 606. As illustrated in FIG. 14 for example, first wet film 602 includes a width W11 and a thickness T11, second wet film 604 includes a width W12 and a thickness T12, and third wet film 606 includes a width W13 and a thickness T13 relative to web 310. Also illustrated in FIG. 14 for example, is a first gap width W14 between the first wet film 602 and the second wet film 604 and a second gap width W15 between the second wet film 604 and the third wet film 606. As discussed in more detail below, the width and thickness of the first, second, and third wet films and the widths of the first and second gap are controlled and modified by the vacuum system 340.

In one form, the discharge rates of first coating material, second coating material 306, and third coating material from the first channel 120, the second channel 122, and the third channel 124 at the discharge end 410 are between about 10.0 mL/min and about 20.0 mL/min. In another more particular form, the discharge rates of first coating material, second coating material 306, and third coating material are between about 12.0 mL/min and about 18.0 mL/min. In another form, the discharge rates of first coating material, second coating material 306, and third coating material from discharge end 410 are between about 15.0 mL/min and about 18.0 mL/min. In any form, the discharge rates of first coating material, second coating material 306, and third coating material from the first channel 120, the second channel 122, and the third channel 124 at the discharge end 410 can be the same or vary from each other. For example, the discharge rate of the first and third coating materials can be the same and the discharge rate of the second coating material 306 can be different from the first and third coating materials. As another example, the discharge rate of the second coating material 306 can be about twice as fast as the discharge rates of the first and third coating materials. Still, other variations for the rate at which first coating material, second coating material 306, and third coating material are discharged from discharge end 410 are also contemplated, and can be dependent on, amongst other things, the desired width and thickness of the first coating material, second coating material 306, and third coating material relative to the particular application of the method and apparatus disclosed herein, and also on the rate at which web 310 is moved relative to slot die head 402. For example, in certain experimental coating processes described in greater detail below in the "EXAMPLES" section of the subject document, the discharge rates of first, second, and third coating materials from the first channel 120, the second channel 122, and the third channel 124 of the slot die shim 100 in the slot die head 402 was between about 0.5 mL/min and about 4.0 mL/min. In one form and in the "EXAMPLES" section of the subject document, the discharge rate of the second coating material from the second channel 122 was 0.843 mL/min and the discharge rate of the first and third coating materials from the first channel 120 and the third channel 124, respectively, was 0.873 mL/min wherein the first and third coating materials were combined in the first reservoir 322.

In the illustrated example of FIG. 14, the targeted width W11 of the first wet film 602 and the targeted width W13 of the third wet film 606 are substantially similar or the same and ranges between about 600 µm and 1500 µm. The targeted width W12 of the second wet film 604 is larger than the targeted width W11 of the first wet film 602. The targeted width W12 of the second wet film 604 is larger than the targeted width W13 of the third wet film 606. The targeted width W12 of the second wet film 604 ranges between about 900 µm and 1700 µm. Also illustrated in FIG. 14 for example is width W14 of a first gap between the first wet film 602 and the second wet film 604 and a width W15 of a second gap between the second wet film 604 and the third wet film 606. The targeted width W14 of the first gap and the targeted width W15 of the second gap are substantially similar or the same and range between about 90 µm and 700 µm. However, it should be appreciated that alternative values for the targeted width W11 of the first wet film 602, targeted width W12 of the second wet film 604, the targeted width W13 of the third wet film 606, and the targeted width W14 of the first gap and the targeted width W15 of the second gap are also contemplated. Additional dimensions for the targeted width W11 and thickness T11 of the first wet film 602, targeted width W12 and thickness T12 of the second wet film 604, the targeted width W13 and thickness T13 of the third wet film 606, and the targeted width W14 of the first gap and the targeted width W15 of the second gap are provided in the "EXAMPLES" section of the subject document.

FIGS. 6 and 8 also illustrate that a first pressure P1 is present downstream of slot die head 402 and that a second pressure P2 is present upstream from slot die head 402. More particularly, first pressure P1 is indicative of ambient air pressure in the atmosphere surrounding apparatus 300, while second pressure P2 is indicative of air pressure in chamber 524 of housing 404. When vacuum system 340 applies a vacuum force to chamber 524, second pressure P2 is less than first pressure P1 and the difference between first pressure P1 and second pressure P2 defines a coating vacuum. In one form, the coating vacuum is between about 0 Pa and about 800 Pa. However, it should be appreciated that other values for the coating vacuum are contemplated and fall within the scope of the subject document.

One factor that can affect the widths and thicknesses of the wet films 602, 604, and 606 is necking of the first coating material, second coating material 306, and third coating material upon exit of the first channel 120, second channel 122, and third channel 124, respectively. Another factor that can affect the widths and thicknesses of the wet films 602, 604, and 606 is the flow rates of the first coating material, second coating material 306, and third coating material through the first channel 120, second channel 122, and third channel 124, respectively. It should be appreciated that the targeted widths W11, W12, and W13 and thicknesses T11, T12, and T13 of wet films 602, 604, and 606 and targeted widths W14 and W15 of the gaps are also regulated and controlled by the amount of vacuum force applied to chamber 524 by vacuum system 340. Adjustments to the coating vacuum can be used to control in real time the targeted width W11 and thickness T11 of the first wet film 602, targeted width W12 and thickness T12 of the second wet film 604, the targeted width W13 and thickness T13 of the third wet film 606, the targeted width W14 of the first gap and the targeted width W15 of the second gap that will be applied to web 310. Further, the ability to control thicknesses T11, T12, and T13 of wet films 602, 604, and 606 in this manner provides an improved approach for achieving and maintaining relative consistency and uniformity in the thicknesses T11, T12, and T13 of wet films 602, 604, and 606 along web 310. Similarly, each of the test elements obtained from web 310 will have a more uniform thickness T of each of the first reagent material, the second reagent material 460, and the third reagent material, thereby resulting in greater lot to lot consistency in the finished test elements.

At a low amount of vacuum force the width W11 of the first wet film 602, width W12 of the second wet film 604, and the width W13 of the third wet film 606 may each be respectively less than the width W1 of the first channel 120, the width W2 of the second channel 122, and the width W3 of the third channel 124 as a result of other factors including but not limited to necking and flow rate. At a higher amount of vacuum force, the width W11 of the first wet film 602, width W12 of the second wet film 604, and the width W13 of the third wet film 606 may each be respectively greater than the width W1 of the first channel 120, the width W2 of the second channel 122, the width W3 of the third channel. In some forms, the vacuum force will change the width W11 of the first wet film 602, width W12 of the second wet film 604, and the width W13 of the third wet film 606 a different amount respectively to the width W1 of the first channel 120, the width W2 of the second channel 122, and the width W3 of the third channel 124. For example, the vacuum force may alter the width W11 of the first wet film 602 and the width W13 of the third wet film 606 a larger amount than the width W12 of the second wet film 604. Generally, larger increases in the amount of vacuum force applied to chamber 524 by vacuum system 340 will generally result in increases to the targeted width W11 of the first wet film 602, targeted width W12 of the second wet film 604, and the targeted width W13 of the third wet film 606. As the targeted widths W11, W12, and W13 of the wet films 602, 604, and 606 increase, the targeted width W14 of the first gap and the targeted width W15 of the second gap decrease. The targeted widths W11, W12, and W13 of wet films 602, 604, and 606 can be increased to a larger distance than their corresponding first channel 120, second channel 122, and third channel 124 by increasing the vacuum force of the vacuum system 340.

Figure 10:
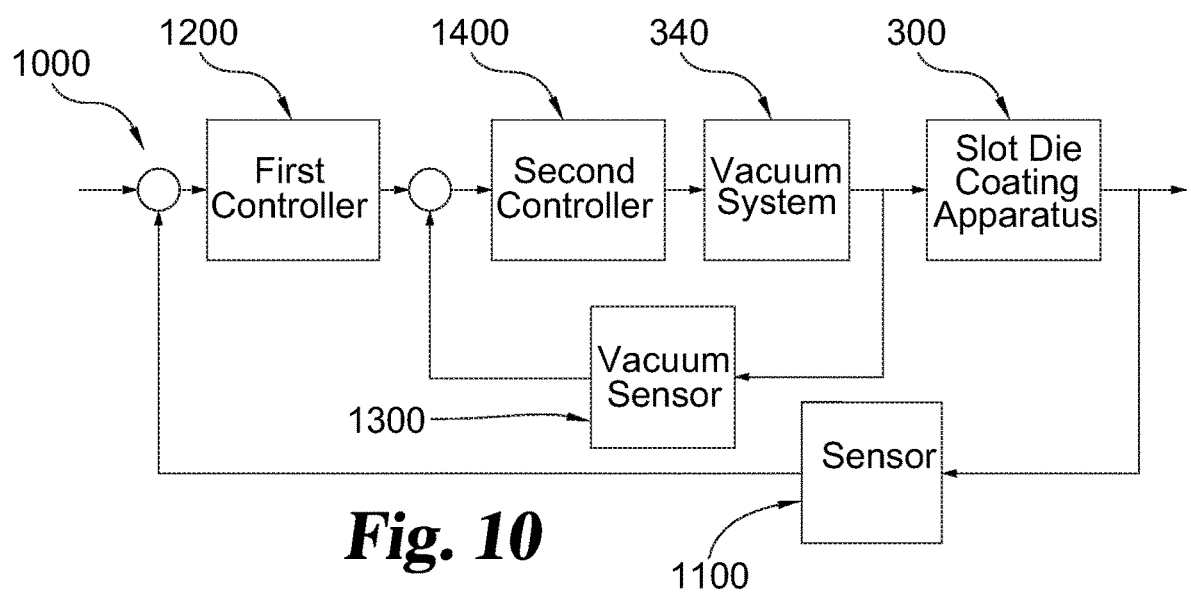
FIG. 10 is a diagrammatic illustration of a system for controlling operation of the slot die coating apparatus of FIG. 3 and vacuum supply system of FIG. 9.

One non-limiting approach for maintaining consistency and uniformity in widths W11, W12, and W13 and thicknesses T11, T12, and T13 of wet films 602, 604, and 606, and widths W14 and W15 of the gaps between wet films 602, 604, and 606 will now be described in connection with the schematic illustration of system 1000 in FIG. 10. More particularly, system 1000 includes apparatus 300, including vacuum system 340, each of which has been described above. System 1000 also includes a sensor 1100 for determining the widths W11, W12, and W13 of wet films 602, 604, and 606, and widths W14 and W15 of the gaps after the films 602, 604, and 606 have been applied to web 310 by apparatus 300. In one form, sensor 1100 can be an optical sensor, such as a digital camera, although other forms for sensor 1100 are contemplated. Sensor 1100 is also operable to generate a sensor signal corresponding to the determined widths W11, W12, and W13 of the wet films 602, 604, and 606, and the widths W14 and W15 of the gaps and transmit the sensor signal to a first controller 1200. A first controller 1200 is programmed to determine if the widths W11, W12, and W13 of the wet films 602, 604, and 606, and the widths W14 and W15 of the gaps determined by sensor 1100 correspond to a value other than a predetermined value or range of values and, if so, transmit a corresponding controller signal to a second controller 1400 indicating the changes that must be made to the width W11 of the first wet film 602, width W12 of the second wet film 604, and the width W13 of the third wet film 606 in order to achieve a targeted thickness T11 of first wet film 302, targeted thickness T12 of second wet film 604, and targeted thickness T13 of third wet film 606 based on the following equation:

$$\text{Thickness } T = (\text{Coating Material Flow Rate})/[(\text{Web Speed})*(\text{Width } W)]$$

By changing the widths W11, W12, and W13 of the wet films 602, 604, and 606, then the widths W14 and W15 of the gaps will also be altered as desired. In one form, the predetermined value for width W for each of the first wet film 602 and the third wet film 606 is from about 500 μm to about 1200 μm and the predetermined value for width W for second wet film 604 is from about 1200 to about 1700 μm. In another form, the predetermined value for width W is 700 μm. In another variation, the predetermined value for width W of the second wet film 604 is about twice as large as the predetermined value for width W of either the first wet film 602 or the third wet film 606. For example, the predetermined value for width W for second wet film 604 is about 9 μm to about 16 μm and the predetermined value for width W for first and third wet films 602 and 606 is about 450 μm to about 800 μm. In another embodiment, the predetermined values for width W for wet films 602, 604, and 606 are minimum value relatives to electrodes positioned on the web 310 of substrate material 312. However, it should be appreciated that other variations in the predetermined value or range of values for width W are possible.

Second controller 1400 is generally programmed to control the amount of vacuum applied by vacuum system 340 in response to receiving from first controller 1200 a controller signal indicating that changes must be made to widths W11, W12, and W13 of the wet films 602, 604, and 606, and widths W14 and W15 of the first and second gaps and/or in response to receiving a sensor signal from vacuum sensor 1300 that is indicative that the actual amount of vacuum being applied to chamber 524 of housing 404 does not correspond to the amount of vacuum that should be applied thereto as determined by controller 1400. In view of the foregoing, it should be appreciated that system 1000 can, by way of non-limiting example, automatically and in real-time control the widths W11, W12, and W13, and in turn thicknesses T11, T12, and T13, of wet films 602, 604, and 606 and widths W14 and W15 of the first and second gaps that are applied to web 310. More particularly, in the event any widths W11, W12, and W13 of wet films 602, 604, and 606 determined by sensor 1100 do not correspond to the predetermined value or range of values, then the amount of vacuum applied by vacuum system 340 will automatically be adjusted as appropriate to bring widths W11, W12, and W13 of wet films 602, 604, and 606 back to the predetermined value or within the range of predetermined values. Amongst other things, automatically adjusting the widths W11, W12, and W13 of wet films 602, 604, and 606 in this manner results in a more uniform and consistent thicknesses T11, T12, and T13, of wet films 602, 604, and 606 along web 310, which in the case of the first reagent material, second reagent material 460, and the third reagent material, results in greater consistency between the individual test elements that will be obtained from web 14 to which wet films 602, 604, and 606 are applied. Moreover, adjusting the widths W11, W12, and W13 of wet films 602, 604, and 606 in this manner also results in adjusting the widths W14 and W15 of the first and second gaps.

It has also been discovered that controlling the amount of vacuum applied to chamber 524 can significantly adjust the widths W11, W12, and W13 and thicknesses T11, T12, and T13, of wet films 602, 604, and 606. It was discovered that controlling the amount of vacuum applied to the chamber 524 causes spreading or increasing of widths W11, W12, and W13 of the wet films 602, 604, and 606 and decreasing thicknesses T11, T12, and T13, of wet films 602, 604, and 606. The widths W11, W12, and W13 of the wet films 602, 604, and 606 can be modified to correspond with the widths W1, W2, and W3 of the channels 120, 122, and 124. In other forms, the widths W11, W12, and W13 of the wet films 602, 604, and 606 can be less than or greater than the widths W1, W2, and W3 of the channels 120, 122, and 124. Also, controlling the amount of vacuum applied to chamber 524 results in a more uniform thickness profile of the first reagent material, second reagent material 460, and the third reagent material across the widths of each of these reagent layers formed after wet films 602, 604, and 606 dry.

In addition, it should also be appreciated that adjusting the widths W11, W12, and W13 and thicknesses T11, T12, and T13, of wet films 602, 604, and 606 by controlling the amount of vacuum applied to chamber 524 also eliminates any need to move slot die head 402 relative to web 310 such that a constant coating gap CG can be maintained between said slot die head 402 and web 310 as first coating material, second coating material 306, and the third coating material are applied thereto. Furthermore, a constant flow rate of first coating material, the second coating material 306, and the third coating material through slot die head 402 and a constant speed of web 310 relative to slot die head 402 can also be maintained when the widths W11, W12, and W13 and thicknesses T11, T12, and T13 of wet films 602, 604, and 606 are adjusted by controlling the amount of vacuum applied to chamber 524. Likewise, the approach described herein conveniently only requires a change to be made to a single process parameter in order to adjust the widths W11, W12, and W13 and thicknesses T11, T12, and T13 of wet films 602, 604, and 606.

While not previously discussed, it should be appreciated that slot die coating apparatus 300 and/or system 1000 can be provided with additional features useful for processing web 310 either before or after the formation of wet films 602, 604, and 606. For example, in one form, apparatus 300 also includes a dryer or drying mechanism that facilitates drying of wet films 602, 604, and 606 to form layers of the first reagent material, second reagent material 460, and the third reagent material. In one aspect, the dried layers of the first reagent material, second reagent material 460, and the third reagent material each include a thickness relative to substrate material 312 between about 1 μm and about 20 μm, between about 3 μm and about 20 μm, or between about 2 μm and about 10 μm, although other values for the thicknesses of the dried layers of the first reagent material, second reagent material 460, and the third reagent material are also contemplated. Apparatus 300 may also include one or more cleaners or other components for preparing and/or processing web 310 for application of first coating material, second coating material 306, and the third coating material. Apparatus 300 may also include additional devices or components for preparing and/or processing web 310 to form a plurality of test elements. For example, additional rollers carrying webs that can form additional layers of material for the plurality of test elements can also be included. One or more cutting devices can also be included with apparatus 300 to cut web 310 into the plurality of test elements following the formation and drying of wet films 602, 604, and 606. Additionally the cutting devices may cut web 310 and one or more of the wet films 602, 604, and 606 into the plurality of test elements. In one form, the web 310 is cut by the cutting devices through the second wet film 604 to form the plurality of test elements. In this embodiment, the width W12 of second wet film 604 is sufficient to cover one or more electrodes on each of the plurality of test strips and the first film 602 is positioned on a first group of test strips and the third film 606 is positioned on a second group of test strips wherein the first group of test strips does not include any test strips with the third film 606 thereon. In one form, the test elements include a length between about 20 millimeters and about 50 millimeters and a width between about 5 millimeters and about 15 millimeters. In a more particular form, the test elements include a length between about 33 millimeters and about 38 millimeters and a width between about 7 millimeters and about 9 millimeters.

As indicated above, the foregoing description regarding the application of first coating material, second coating material 306, and the third coating material has been made in connection with the formation of first wet film 602 of the first reagent material, second wet film 604 of second reagent material 460, and third wet film 606 of the third reagent material on web 310 of substrate material 312 from which a plurality of test elements will be obtained. Once formed, the test elements can be used in a system that is useful for assessing a different analyte for each reagent material in a sample fluid. In one form, the analyte assessment may range from detecting the presence of the analyte to determining the concentration of the analyte. The analyte and the sample fluid may be any for which the test system is appropriate. By way of non-limiting example, one embodiment is described below in which a first analyte is glucose, a second analyte is ketone, and a third analyte is glucose and the sample fluid is blood or interstitial fluid. However, the assessment of other analytes in different sample fluids is also contemplated.

The test elements provide an electrochemical sensor including a sample-receiving chamber for the sample fluid, and any number of the first reagent material, second reagent material, and the third reagent material that are suitable for producing a first, second, and/or third electrochemical signal in the presence of the test analyte. In one example embodiment, a first test element can include the first reagent material and the second reagent material and a second test element can include the second reagent material and the third reagent material. In one form, the test elements are in the form of disposable test strips. The test elements are used in combination with a meter for determination of the analyte in the sample fluid. The meter conventionally includes a connection with electrodes on the test elements and circuitry to evaluate the electrochemical signal corresponding to the concentration of one or more analytes. The meter may also include means for determining that the sample fluid has been received by the test element and that the amount of sample fluid is sufficient for testing. The meter typically will store and display the results of the analysis, or may alternatively provide the data to a separate device. It will be appreciated by those of skill in the art that optical sensors (i.e. sensors configured with reagent material to produce an optical signal in the presence of an analyte) may also be produced according to the teachings herein, analogously to electrochemical sensors.

As indicated above, the foregoing description regarding the resultant width W14 of the first gap between the first wet film 602 and the second wet film 604 and the width W15 of the second gap between the second wet film 604 and the third wet film 606 from which a plurality of test elements will be obtained each provide a region on an electrode without reagent material. Once formed, the test elements can also be used in a system that is useful or beneficial in some measurement methods for example such as impedance and capacitance for detecting a response to be used to correct for interfering variables such as temperature, hematocrit, and/or other potential electrochemically active species not associated with the analytes of interest. If the widths W14 and W15 of the gaps are nominal or almost zero, then the adjacent wet films are substantially in contact or touching each other and crossreactivity is typically reduced. Crossreactivity is whether or not a signal produced by a first analyte interferes with the signal of a second adjacent analyte. Crossreactivity is any phenomenon by which a signal from the first analyte creates an undesired effect on the second or any other analyte. As such, the crossreactivity deals with chemical interferences between the analytes. This can result in artificially elevated signals and presents a major issue when analyzing low signal samples adjacent to high signal samples. Surprisingly it was discovered that for some types of reagents such as reagents having high viscosity at low shear, two reagents positioned substantially in contact with each other on a test strip, i.e., no gap, have less crossreactivity than two reagents that have a small gap between them. Beneficially it was also discovered that for some types of reagents such as reagents having high viscosity at low shear, two reagents positioned substantially in contact with each other on a test strip, i.e., no gap, prevent diffusion, mixing, or spreading of the reagents. Examples of reagents with high viscosity at low shear include reagents with a viscosity of between about 95 to 115 mPa-s and a surface tension of between about 33 and 42 mN/m. Other formulations of reagents may have different properties.

It is contemplated that the test elements may be useful for the determination of a wide variety of analytes. For example, the test elements may be readily adapted for use with the first reagent material, second reagent material, and the third reagent material having any suitable chemistry that can be used to assess the presence of the analyte. In one specific form, the test elements are configured and used for the testing of one or more analytes in a biological fluid. Such analytes may include, for example, glucose, cholesterol, HDL cholesterol, triglycerides, lactates, lactate dehydrogenase, alcohol, uric acid, and ketone. As used herein, "ketone" means ketone bodies such as hydroxybutyrate, especially 3-hydroxybutric acid. Non-limiting examples of biological fluids in which the analyte can be assessed include any bodily fluid in which the analyte can be measured, such as interstitial fluid, dermal fluid, sweat, tears, urine, amniotic fluid, spinal fluid and blood. The term "blood" in the context of this document includes whole blood and its cell-free components, namely plasma and serum. When the test elements are configured for the testing of glucose, the sample fluid may specifically include, for example, fresh capillary blood obtained from the fingertip or approved alternate sites (e.g., forearm, palm, ear lobe, upper arm, calf and thigh), and fresh venous blood. In addition, the test elements may also be useful in connection with control fluids that are used in conventional fashion to verify the integrity of the system for testing.

The bodily fluid containing the one or more analytes to be assessed may be acquired and delivered to the test elements in any fashion. For example, a blood sample may be obtained in conventional fashion by incising the skin, such as with a lancet, and then contacting the test element with fluid that appears at the skin surface. In one aspect, the test elements are operable for assessing the targeted analytes with only using very small fluid samples. Similarly, in one aspect, only a slight skin incision is necessary to produce the volume of fluid required for the test, and the pain and other concerns with such a method can be minimized or eliminated.

The test elements which are formed from web 310 on which the layers of the first reagent material, second reagent material 460, and the third reagent material are deposited include several basic components. More particularly, the test elements comprise a small body defining a chamber in which the sample fluid is received for testing. This "sample-receiving chamber" may be filled with the sample fluid by suitable means, such as by capillary action, but also optionally assisted by pressure or vacuum. The sample-receiving chamber includes electrodes and chemistry suitable for producing an electrochemical signal indicative of one or more analytes in the sample fluid.

Figure 13A:
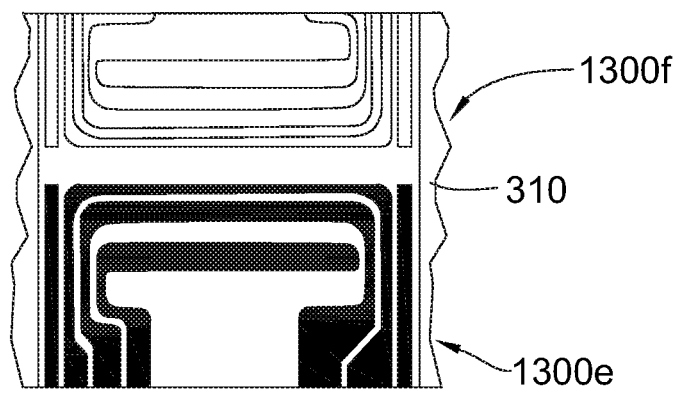
FIG. 13 is a schematic representation in two steps (A-B) how two electrochemical test elements with three reagent zones without gaps between the reagent zones are manufactured using the slot-die coating process of the present application.
Figure 13B:
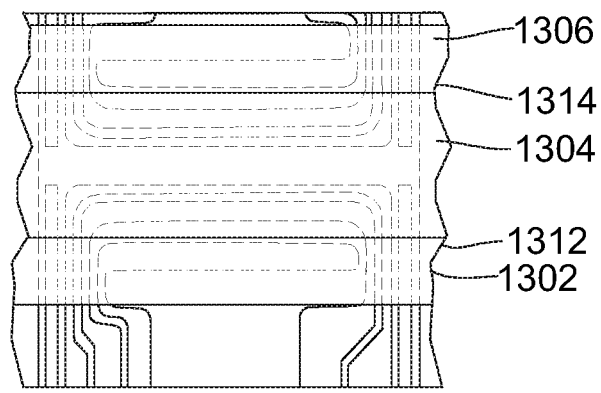

Referring now to FIGS. 11, 12, and 13 for example, a portion of web 310 is illustrated and includes a plurality of electrode systems 1300 *a-f* which will individually be included on separate test elements formed from the illustrated portion of web 310. Each of the electrode systems 1300 *a-f* includes a plurality of electrodes and electrode traces which terminate in contact pads (not illustrated). The electrode systems 1300 *a-f* are arranged in a head-to-head or nose-to-nose configuration for manufacturing. The electrode systems 1300 *a-f* can be arranged in alternative configurations. A portion of a layer 1302 of the first reagent material overlies at least a portion of each of the electrode systems 1300 *a, c, e*. A portion of a layer 1304 of second reagent material 460 overlies a portion of each of the electrode systems 1300 *a-f*. A portion of a layer 1306 of the third reagent material overlies a portion of each of the electrode systems 1300 *b, d, f*. Similarly, it should be appreciated that the first reagent material, second reagent material 460, and the third reagent material are applied to web 310 following the formation of electrode systems 1300 *a-f* thereon. As also illustrated in FIGS. 11, 12, and 13, reagent layers 1302, 1304, and 1306 extend as narrow, substantially parallel, stripes along the length of the illustrated portion of web 310 and across the corresponding electrode systems 1300 *a-f*. In the illustrated embodiments, after the web 310 is cut to form individual test strips, each of the electrode systems 1300 *a-f* will include two reagent layers. For example, electrode systems 1300*a, c,* and *e* will each include reagent layer 1302 and reagent layer 1304. Electrode systems 1300*b, d,* and *f* will each include a reagent layer 1306 and reagent layer 1304. In this embodiment, reagent layer 1304 covers portions of all of the electrode sets. In other configurations, any of reagent layers 1302, 1304, and 1306 can be configured and arranged to cover one or more electrode systems.

As mentioned above and illustrated in FIGS. 11, 12, and 13, the reagent layers 1302, 1304, and 1306 extend as narrow, substantially parallel, stripes along the length of the illustrated portion of web 310 and across the corresponding electrode systems 1300 *a-f*. The reagent layers 1302 and 1304 form a first gap 1312 that spans between the reagent layers 1302 and 1304 along the length of the web 310. The reagent layers 1304 and 1306 form a second gap 1314 that spans between the reagent layers 1304 and 1306 along the length of the web 310. The width of each of the first and second gaps 1312 and 1314 can be any configuration. The widths of the first and second gaps 1312 and 1314 can range from between 0 µm to about 600 µm. It should be appreciated that widths of the first and second gaps 1312 and 1314 of about 0 µm corresponds to the adjacent reagent layers fully in contact with each other as illustrated in FIG. 13. It should be appreciated that the largest widths of the first and second gaps 1312 and 1314 of about 600 µm corresponds to the adjacent reagent layers being the furthest distance from one another as illustrated in FIG. 11. Other embodiments can include a greater width of the first and second gaps 1312 and 1314. The first and second gaps 1312 and 1314 provide regions on the electrode sets 1300 *a-f* that do not have reagent layers thereon. The widths of the reagent layers 1302, 1304, and 1306 and the widths of the first and second gaps 1312 and 1314 are further determined based on the orientation and location of the electrode systems 1300 *a-f* on web 310.

In FIGS. 11, 12, and 13, the electrode sets 1300 *a-f* are arranged in a nose-to-nose configuration wherein each of the electrode sets 1300 *a-f* includes a combined counter/reference electrode and a working electrode. In these embodiments, the reagent layers 1302 and 1306 are each positioned on a working electrode and reagent layer 1304 is positioned on a combined counter/reference electrode. Other embodiments can include a different arrangement of electrode sets and a different arrangement or number of reagent layers.

Substrate material 312 of web 310 is formed of an insulating material on which electrode systems 1300 *a-f* are positioned. Typically, plastics such as vinyl polymers, polyimides, polyesters, and styrenes provide the electrical and structural properties which are required. Further, because the test elements can be mass producible from rolls of material, it is desirable that the material properties be appropriate to have sufficient flexibility for roll processing, while also giving a useful stiffness to the finished element. Substrate material 312 can be selected as a flexible polymeric material such as polyester, including high temperature polyester materials; polyethylene naphthalate (PEN); and polyimide, or mixtures of two or more of these. Polyimides are available commercially, for example under the trade name Kapton®, from E.I. duPont de Nemours and Company of Wilmington, Del. (duPont). One specific possibility for substrate material 312 is MELINEX® 329 available from duPont.

The test elements are configured to detect the presence of, and/or measure the concentration of, one or more analytes by way of electrochemical oxidation and reduction reactions. These reactions are transduced to an electrical signal that can be correlated to an amount or concentration of the analyte. Similarly, the electrode system on each test element includes a set of measuring electrodes, e.g., at least a working electrode and a counter electrode, or a combined counter/reference electrode and a working electrode that are positioned within the sample-receiving chamber. The sample-receiving chamber is configured such that sample fluid entering the chamber is placed in electrolytic contact with both the working electrode and the counter electrode. This allows electrical current to flow between the measuring electrodes to affect the electrooxidation or electroreduction of the analyte.

A "working electrode" is an electrode at which the analyte is electrooxidized or electroreduced with or without the agency of a redox mediator, while the term "counter electrode" refers herein to an electrode that is paired with the working electrode and through which passes an electrical current equal in magnitude and opposite in sign to the current passed through the working electrode. The term "combined counter/reference electrode" is meant to include counter electrodes which also function as reference electrodes (i.e., counter/reference electrodes).

The counter and reference electrodes, and the remaining portions of the electrode system, may be formed from a variety of materials. In one aspect, the electrodes should have a relatively low electrical resistance and should be electrochemically inert over the operating range of the test elements. Suitable conductors for the working electrode include gold, palladium, platinum, carbon, titanium, ruthenium dioxide, indium tin oxide, and iridium, as well as others. The counter electrode may be made of the same or different materials, e.g., silver/silver chloride. In one specific embodiment, the counter and reference electrodes are both gold electrodes.

The electrodes may be applied to substrate material 312 in any fashion that yields electrodes of adequate conductivity and integrity. Exemplary processes include sputtering and printing, just to provide a few non-limiting possibilities. In one specific form, gold electrodes are provided by coating substrate material 312 and then removing selected portions of the coating to yield the electrode system. One particular method for removing portions of the coating includes laser ablation or broad field laser ablation.

Laser ablative techniques typically include ablating a single metallic layer or a multi-layer composition that includes an insulating material and a conductive material, e.g., a metallic-laminate of a metal layer coated on or laminated to an insulating material. The metallic layer may contain pure metals, alloys, or other materials, which are metallic conductors. Examples of metals or metallic-like conductors include: aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and alloys or solid solutions of these materials. In one aspect, the materials are selected to be essentially unreactive to biological systems, non-limiting examples of which include gold, platinum, palladium, iridium, silver, or alloys of these metals or iridium tin oxide. The metallic layer may be any desired thickness which, in one particular form, is about 500 nm.

The electrode system may have a variety of configurations suited to the operation of the test elements and corresponding meter. In one form, the counter and reference electrodes are positioned and dimensioned to minimize the volume of sample fluid required to cover them. In addition, the electrodes may also be configured to maintain a current flux of sufficient magnitude as to be measurable using a relatively inexpensive hand-held meter.

The electrode traces and contact pads of the electrode system may be provided in a variety of fashions consistent with their intended function relative to the test element. These components of the electrode system may be composed of the same material as the electrodes, and are applied to the base substrate in the same manner and simultaneously with the application of the electrodes. In one specific embodiment, the traces and contact pads are gold, and are formed by laser ablation. However, alternate materials and methods of application may be employed.

Each of the first reagent material, second reagent material 460, and the third reagent material is operable to react with the test analyte to produce the electrochemical signal that represents the presence of the analyte in the sample fluid. The first reagent material, second reagent material 460, and the third reagent material can be configured to react with the same test analyte or different test analytes. For example, the first reagent material can react with a first test analyte and second reagent material 460 can react with a second test analyte wherein the first test analyte is different than the second test analyte. In one form, the first and the third reagent materials can react with the same test analyte and second reagent material 460 can react to a different test analyte. In another form, first and the third reagent materials can react with different test analytes. The first reagent material, second reagent material 460, and the third reagent material can include a variety of active components selected to determine the presence and/or concentration of various analytes. The test chemistry is therefore selected in respect to the analyte to be assessed. As is well known in the art, there are numerous chemistries available for use with each of various analytes. For example, in one particular form, the first reagent material, second reagent material 460, and the third reagent material can include one or more enzymes, co-enzymes, and co-factors, which can be selected to determine the presence of glucose in blood. In a more specific form where the analyte is glucose, the active components of the first reagent material, second reagent material 460, and the third reagent material will typically include an oxidoreductase, such as an enzyme for glucose; optionally a co-enzyme or co-factor; and a redox mediator. These components are typically dissolved or suspended in a matrix. The liquid test sample hydrates or dissolves the matrix, and the analyte diffuses through the matrix to react with one or more of the active components. Typically, the enzyme oxidizes the glucose in the test sample to gluconolactone and/or gluconic acid. The mediator, in turn, reacts with or oxidizes the reduced enzyme, and consequently the mediator is reduced in the process. The reduced mediator can be detected at one of the electrodes on the test strip. More specific details regarding a specific form of the first reagent material, second reagent material 460, and the third reagent material for determining the presence of glucose in blood are found in U.S. Pat. Nos. 7,727,467 and/or 7,879,618, the contents of which are incorporated herein by reference in their entireties.

In conventional fashion, the first reagent material, second reagent material 460, and the third reagent material may include a variety of adjuvants to enhance various properties or characteristics thereof. See e.g., U.S. Pat. Nos. 7,727,467 and/or 7,879,618 referred to hereinabove. For example, the first reagent material, second reagent material 460, and the third reagent material may include materials to facilitate the placement of the first reagent material, second reagent material 460, and the third reagent material onto web 310 and to improve its adherence to web 310, or for increasing the rate of hydration of the first reagent material, second reagent material 460, and the third reagent material by the sample fluid. Additionally, the first reagent material, second reagent material 460, and the third reagent material can include components selected to enhance the physical properties of the resulting dried reagent layer, and the uptake of a liquid test sample for analysis. Examples of adjuvant materials to be used with the first reagent material, second reagent material 460, and the third reagent material include thickeners, viscosity modulators, film formers, stabilizers, buffers, detergents, gelling agents, fillers, film openers, coloring agents, and agents endowing thixotropy.

Non-limiting examples of thickeners that may be included in the first reagent material, second reagent material 460, and the third reagent material include (1) starches, gums (e.g., pectin, guar gum, locust bean (carob seed) gum, konjac gum, xanthan gum, alginates, and agar), casein, gelatin, and phycocolloids; (2) cellulose and semi-synthetic cellulose derivatives (carboxymethyl-cellulose, methyl cellulose, hydroxymethylcellulose, hydroxyethylcellulose, methylhydroxyethylcellulose); (3) polyvinyl alcohol and carboxyvinylates; and (4) bentonite, silicates, and colloidal silica. More specific forms of thickeners include a combination of a xanthan gum sold under the trade name Keltrol F by CP Kelco US, Inc., and carboxylmethyl cellulose sold under the trade name AQUALON® CMC 7F PH by Hercules Inc., Aqualon Division.

Film forming and thixotropic agents that can be included in the first reagent material, second reagent material 460, and the third reagent material include polymers and silica. One more specific thixotropic agent includes silica sold under the trade name Kieselsaure Sipemate FK 320 DS by Degussa AG, while a more specific film forming agent includes polyvinylpyrrolidone, sold under the trade name polyvinylpyrrolidone Kollidon 25, by BASF, and polyvinyl propionate dispersion.

Stabilizers for the enzyme in the first reagent material, second reagent material 460, and the third reagent material can be selected from sacchhrides and mono- or di-fatty acid salts. More specific stabilizers include trehalose sold under the trade name D-(+)-Trehalose dihydrate by Sigma Chemical Co. and sodium succinate.

Non-limiting examples of detergents that can be included in the first reagent material, second reagent material 460, and the third reagent material include water-soluble soaps, as well as water-soluble synthetic surface-active compounds such as alkali, earth alkali or optionally substituted ammonium salts of higher fatty acids, e.g., oleic or stearic acid, mixtures of natural fatty acids, for example, from coconut or tallow oil, fatty sulphates, esters of sulphonic acids, salts of alkyl sulphonic acids taurine salts of fatty acids, fatty acid amides, and ester amides. More specific forms of detergents include an ester amide, n-octanoyl-N-methylglucamide, sold under the trade name Mega-8 by Dojindo Molecular Technologies, Inc., and a fatty acid salt, N-methyl oleyl taurate sodium salt, sold under the trade name Geropon T77 by Rhodia HPCII (Home, Personal Care and Industrial Ingredients).

In one form, the first reagent material, second reagent material 460, and the third reagent material are formulated as a viscous solution that includes thickeners and thixotropic agents to enhance the physical properties of reagent layers 1302, 1304, and 1306. The thickeners are selected to provide a thick, liquid matrix having the remaining components homogeneously dispersed therein. The thickening and thixotropic agents also inhibit the liquid or semi-paste material from running or spreading over the surface of web 310 after it has been deposited and before it dries. After the first reagent material, second reagent material 460, and the third reagent material are deposited, it quickly dries to a readily hydratable matrix.

The following examples are for illustration purposes and are not to be construed as limiting the invention disclosed in this document to only the embodiments disclosed in these examples.

Example I

Figure 15:
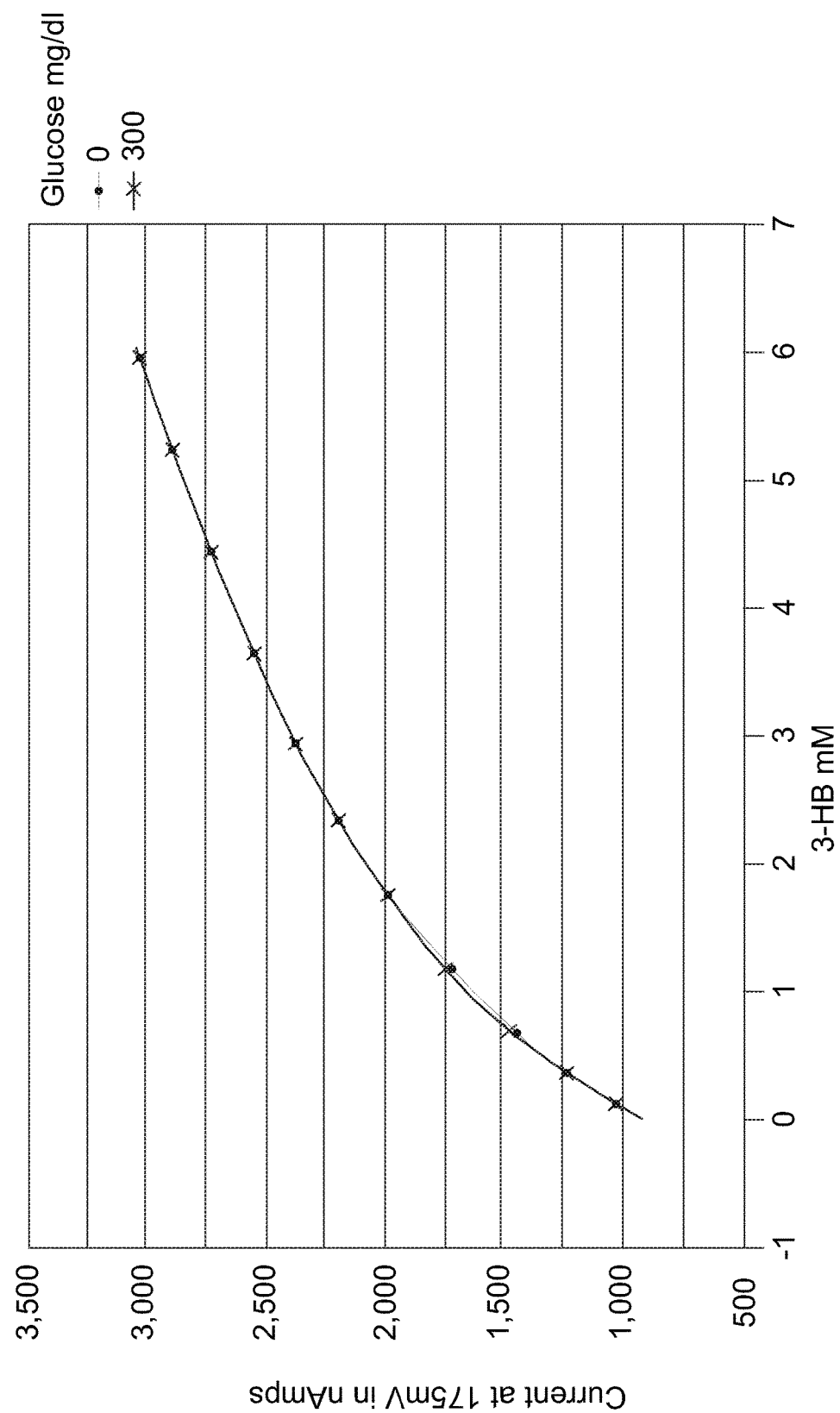
FIG. 15 shows the dose-response results of an electrochemical test element with two reagents.

FIG. 15 illustrates the aqueous dose response of a test sensor that includes two reagent layers, such as reagent layer 1302 and reagent layer 1304, wherein reagent layer 1302 is positioned on a working electrode and reagent layer 1304 is positioned on a combined counter/reference electrode as illustrated in FIG. 12. In this embodiment, reagent layer 1302 is configured for testing for the analyte, 3-hydroxybutric acid (ketone bodies), and reagent layer 1304 is configured for testing for the analyte, glucose, in the presence of two different concentrations of glucose. The first concentration of glucose is 0 mg/dl and the second concentration of glucose is 300 mg/dl. The graph in FIG. 15 demonstrates the absence of interference between the two different reagent layers, such as reagent layer 1302 and reagent layer 1304.

Example II

The following examples are being provided to illustrate the relationship between the widths of the reagent layers, widths of the gaps between the reagent layers, widths of the channels on the slot die shim, widths of the divider walls on the slot die shim, flow rate of reagent layers, and vacuum parameters associated with the application of the first reagent material, second reagent material 460, and the third reagent material to web 310. The combined flow rate of the first reagent layer and the third reagent layer was 0.873 mL/minute. The flow rate of the second reagent layer was 0.846 mL/min. Each of the Examples A-C discussed below indicates the vacuum must be applied to obtain a desired thickness T and width W (FIG. 13) of each of the first wet film 602, second wet film 604, and third wet film 606. In each of the Examples A-C, the vacuum was applied to attempt to obtain the desired width W of the first wet film 602 to correspond with the width W1 of the first channel 120. Similarly the vacuum was applied to attempt to obtain the desired width W of the second wet film 604 to correspond with the width W2 of the second channel 122. The vacuum was applied to attempt to obtain the desired width W of the third wet film 606 to correspond with the width W3 of the third channel 124. The target wet film thickness was 55 μm and the target dry thickness was 5 μm.

Example A

Figure 16:
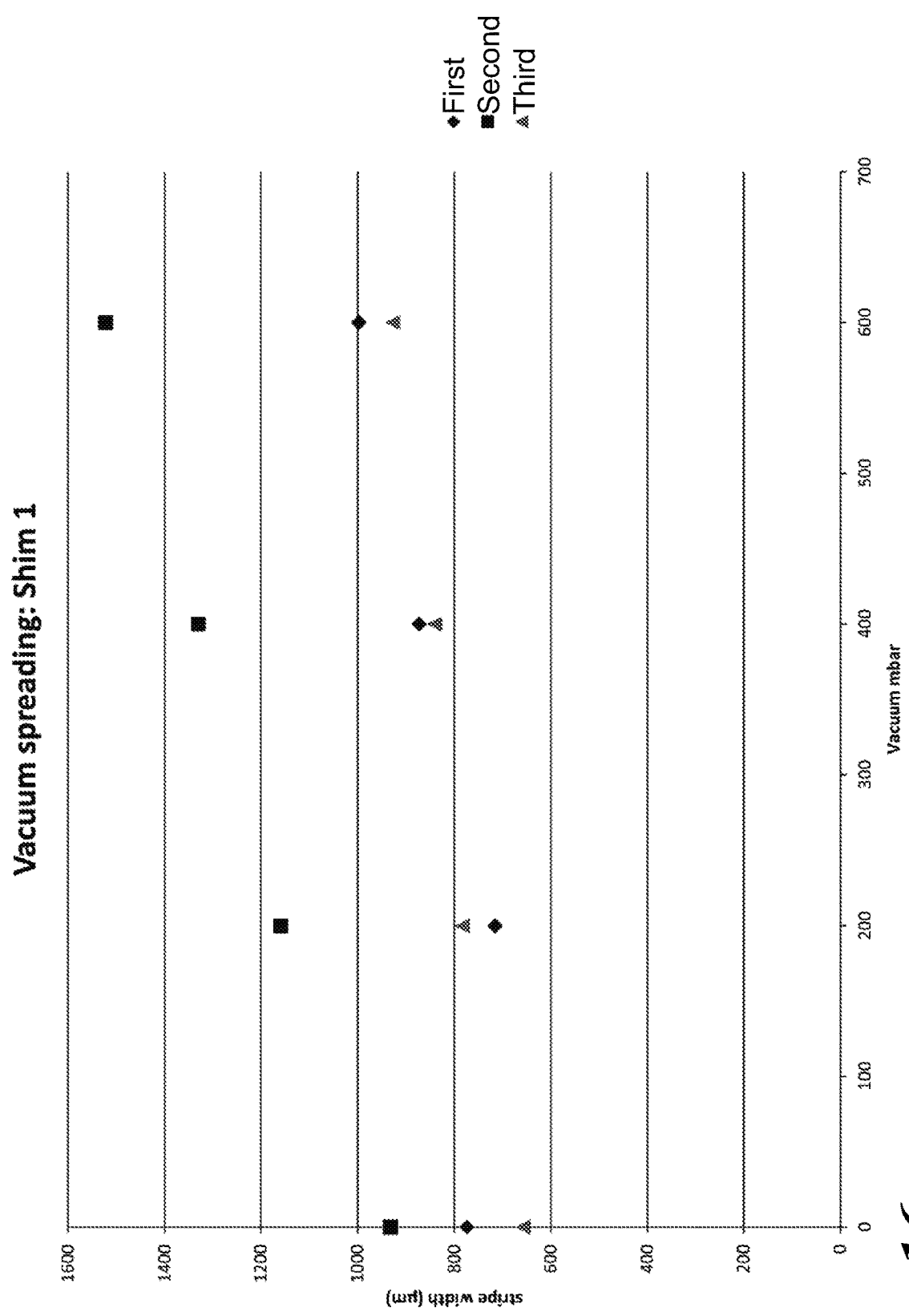
FIG. 16 is a graph of the actual spreading of a first wet film, a second wet film, and a third wet film applied to a substrate upon application of a vacuum with the use of a first slot die shim.

In Example A, the actual spreading of the wet films upon application of a vacuum is measured and displayed graphically in FIG. 16. The slot die shim used in the testing had a width W1 of the first channel 120 of 800 µm, the width W2 of the second channel 122 was 1550 µm, and the width W3 of the third channel 124 was 790 µm. The slot die shim also had a width W4 of the first divider wall 126 of 103 µm and the width W5 of the second divider wall 128 was 121 µm. In the table labeled "Actual Spreading", the widths of the first, second, and third wet films and the widths of the first and second gaps were measured under an increasing vacuum force. As the vacuum increased from 0 Pa to about 200 Pa the widths W11, W12, and W13 of the first, second, and third wet films were all less than the widths of their respective channels 120, 122, and 124. At a vacuum of 400 Pa the widths W11 and W13 of the first and third wet films were greater than the widths W1 and W3 of their corresponding channels 120 and 124, and the width W12 of the second film was less than the width W2 of the second channel 122. At a vacuum of 600 Pa, the widths W11, W12, and W13 of the first, second, and third wet films were greater than the widths W1, W2, and W3 of the respective channels 120, 122, and 124. At a vacuum between 0 Pa and 400 Pa, the width W14 of the first gap and the width W15 of the second gap were larger than the width W4 of the first divider wall 126 and the width W5 second divider wall 128, respectively.

| Actual Spreading | | | | |
| --- | --- | --- | --- | --- |
| Vacuum (Pa) | 0 | 200 | 400 | 600 |
| Width W11 of First Wet Film (µm) | 774 | 715 | 873 | 998 |
| Width W12 of Second Wet Film (µm) | 932 | 1159 | 1330 | 1523 |
| Width W13 of Third Wet Film (µm) | 656 | 783 | 840 | 927 |
| Width W14 of First Gap (µm) | 433 | 303 | 248 | 142 |
| Width W15 of Second Gap (µm) | 494 | 374 | 210 | 111 |

Figure 17:
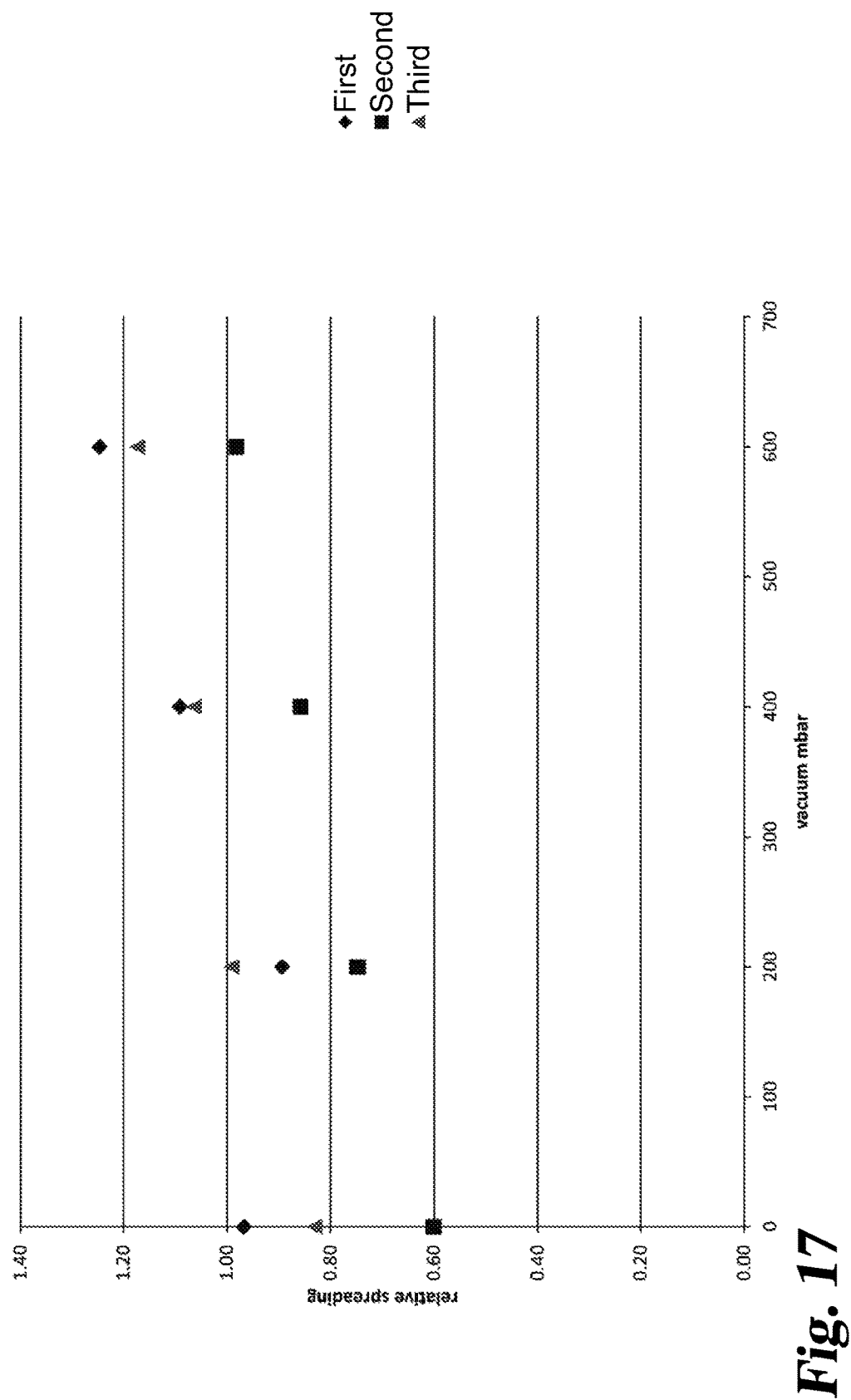
FIG. 17 is a graph of ratios of the width of the wet film to the corresponding width of the channel at each vacuum pressure from FIG. 16.

The table "Relative Spreading" includes the ratio of the width of wet film to the corresponding width of the channel is determined at each vacuum pressure to determine the relative spreading of the wet film upon application of the vacuum. The results are displayed graphically in FIG. 17. The table also determines the ratio of the width of the measured gap to the corresponding width of the divider wall.

| Relative Spreading | | | | |
| --- | --- | --- | --- | --- |
| Vacuum (Pa) | 0 | 200 | 400 | 600 |
| First Channel | 0.97 | 0.89 | 1.09 | 1.25 |
| Second Channel | 0.60 | 0.75 | 0.86 | 0.98 |
| Third Channel | 0.83 | 0.99 | 1.06 | 1.17 |
| First Gap | 433 | 303 | 248 | 142 |
| Second Gap | 494 | 374 | 210 | 111 |

Example B

Figure 18:
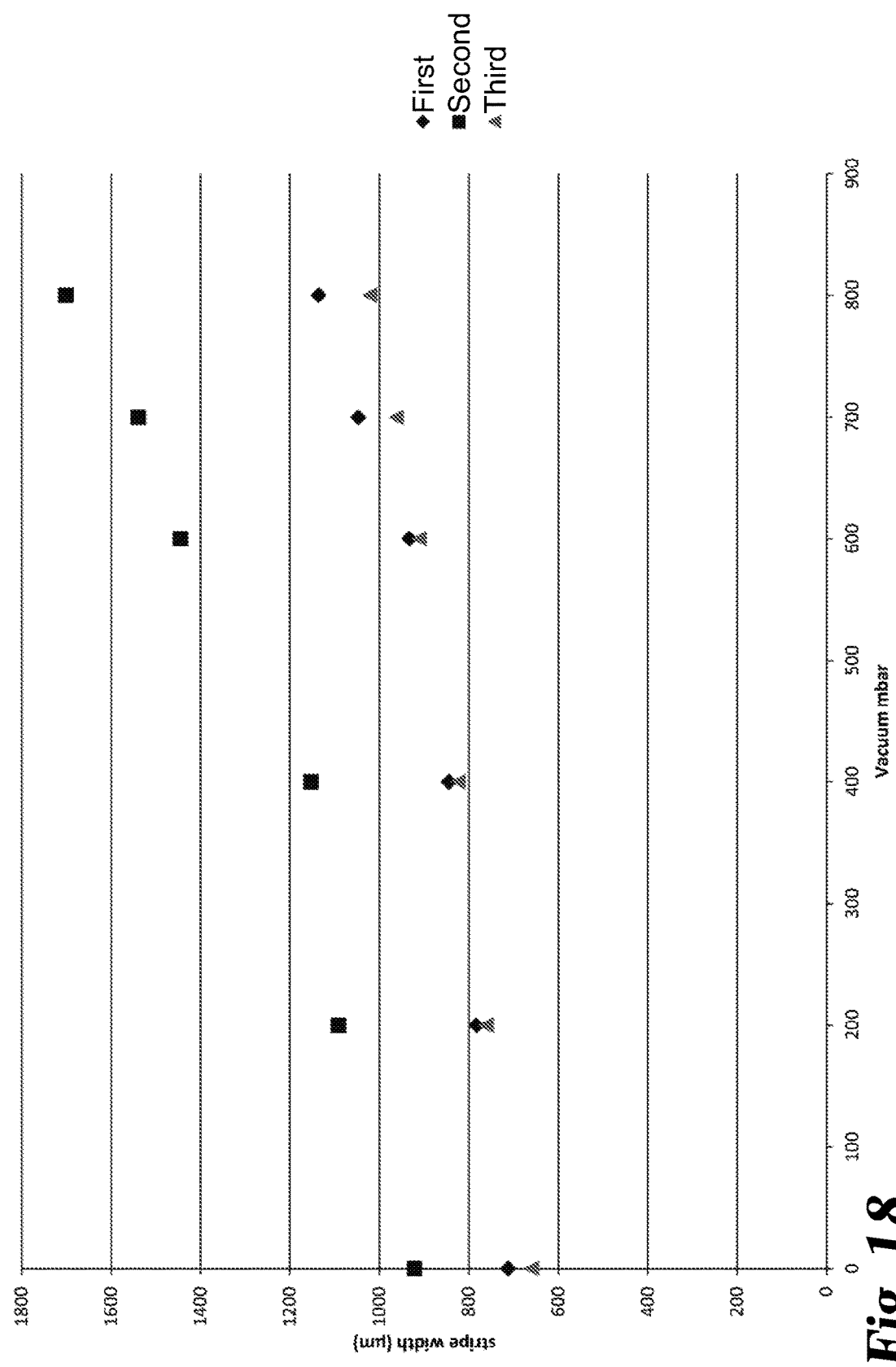
FIG. 18 is a graph of the actual spreading of a first wet film, a second wet film, and a third wet film applied to a substrate upon application of a vacuum with the use of a second slot die shim.

In Example B, the actual spreading of the wet films upon application of a vacuum is measured and displayed graphically in FIG. 18. In Example B, the slot die shim used in the testing had a width W1 of the first channel 120 of 821 µm, the width W2 of the second 122 was 1200 µm, and the width W3 of the third channel 124 was 826 µm. The slot die shim used in testing also had a width W4 of the first divider wall 126 of 379 µm and the width W5 of the second divider wall 128 was 392 µm. In the table labeled "Actual Spreading", the widths of the first, second, and third wet films and the widths of the first and second gaps were measured under an increasing vacuum force. As the vacuum increased from 0 Pa to about 200 Pa the widths W11, W12, and W13 of the first, second, and third wet films were all less than the widths of their respective channels 120, 122, and 124. At a vacuum of 400 Pa the widths W11 and W13 of the first and third wet films were greater than the widths W1 and W3 of their corresponding channels 120 and 124, and the width W12 of the second film was less than the width W2 of the second channel 122. At a vacuum from about 600 Pa to 800 Pa, the widths W11, W12, and W13 of the first, second, and third wet films, were greater than the widths W1, W2, and W3 of the respective channels 120, 122, and 124. At a vacuum between 0 Pa and 200 Pa, the width W14 of the first gap and the width W15 of the second gap were larger than the width W4 of the first divider wall 126 and the width W5 of the second divider wall 128, respectively. As the vacuum increased to 400 Pa, the width W14 of the first gap was larger than the width W4 of the first divider wall 126 and the width W15 of the second gap was smaller than the width W5 of the second divider wall 128. As the vacuum increased from 600 to 800 Pa, the width W14 of the first gap and the width W15 of the second gap were each larger than the width W4 of the first divider wall 126 and the width W5 of the second divider wall 128, respectively.

| Actual Spreading | | | | | | |
| --- | --- | --- | --- | --- | --- | --- |
| Vacuum (Pa) | 0 | 200 | 400 | 600 | 700 | 800 |
| Width W1 of First Wet Film (µm) | 712 | 783 | 845 | 933 | 1047 | 1136 |
| Width W2 of Second Wet Film (µm) | 922 | 1091 | 1153 | 1445 | 1540 | 1701 |
| Width W3 of Third Wet Film (µm) | 660 | 762 | 824 | 910 | 962 | 1022 |
| Width W4 of First Gap (pm) | 676 | 554 | 531 | 350 | 258 | 187 |
| Width W5 of Second Gap (µm) | 558 | 433 | 337 | 169 | 152 | 94 |

Figure 19:
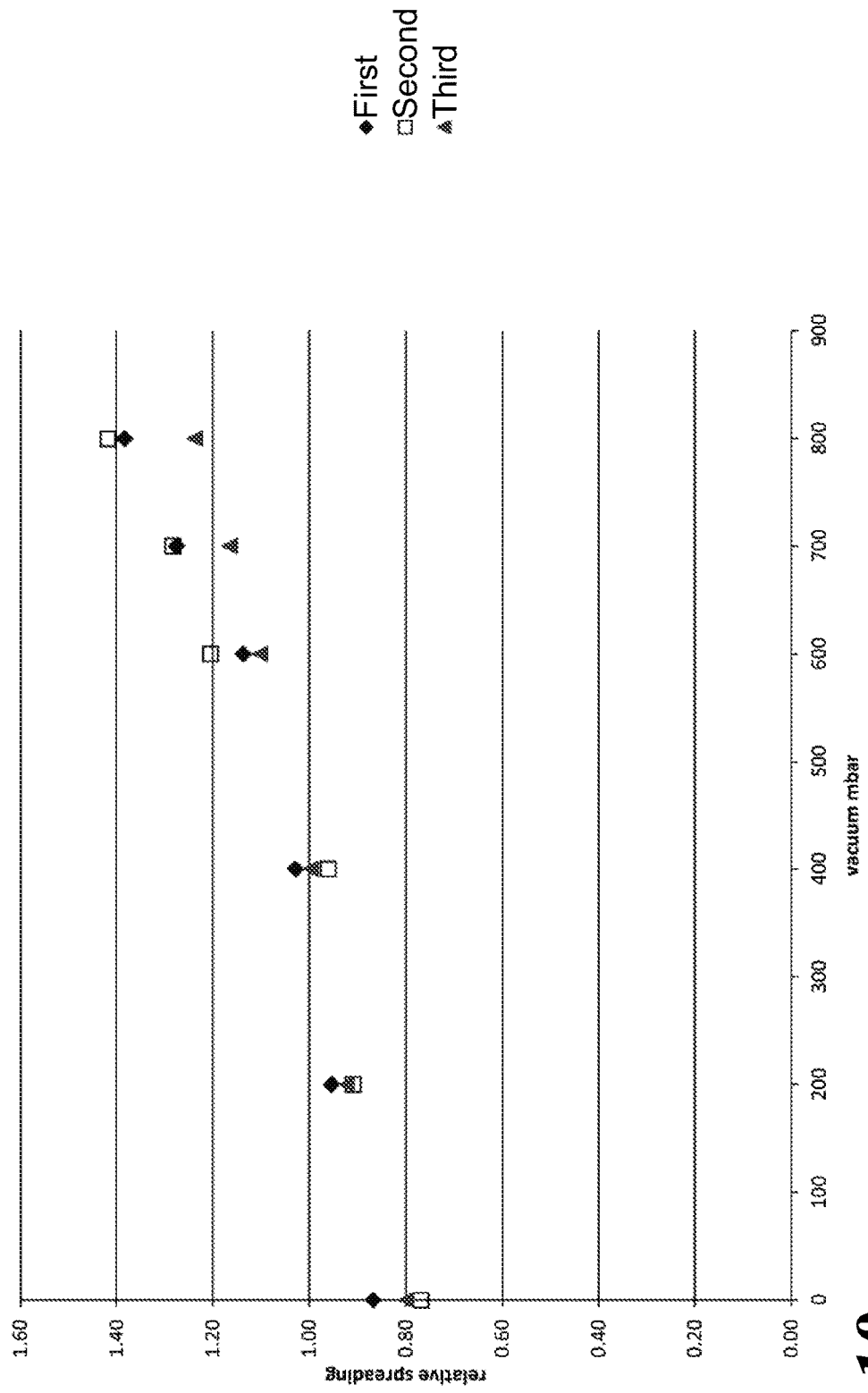
FIG. 19 is a graph of ratios of the width of the wet film to the corresponding width of the channel at each vacuum pressure from FIG. 18.

The table "Relative Spreading" includes the ratio of the width of wet film to the corresponding width of the channel is determined at each vacuum pressure to determine the relative spreading of the wet film upon application of the vacuum. The results are displayed graphically in FIG. 19.

| Relative Spreading | | | | | | |
| --- | --- | --- | --- | --- | --- | --- |
| Vacuum (Pa) | 0 | 200 | 400 | 600 | 700 | 800 |
| First Channel | 0.87 | 0.95 | 1.03 | 1.14 | 1.28 | 1.38 |
| Second Channel | 0.77 | 0.91 | 0.96 | 1.20 | 1.28 | 1.42 |
| Third Channel | 0.80 | 0.92 | 1.00 | 1.10 | 1.16 | 1.24 |

Example C

Figure 20:
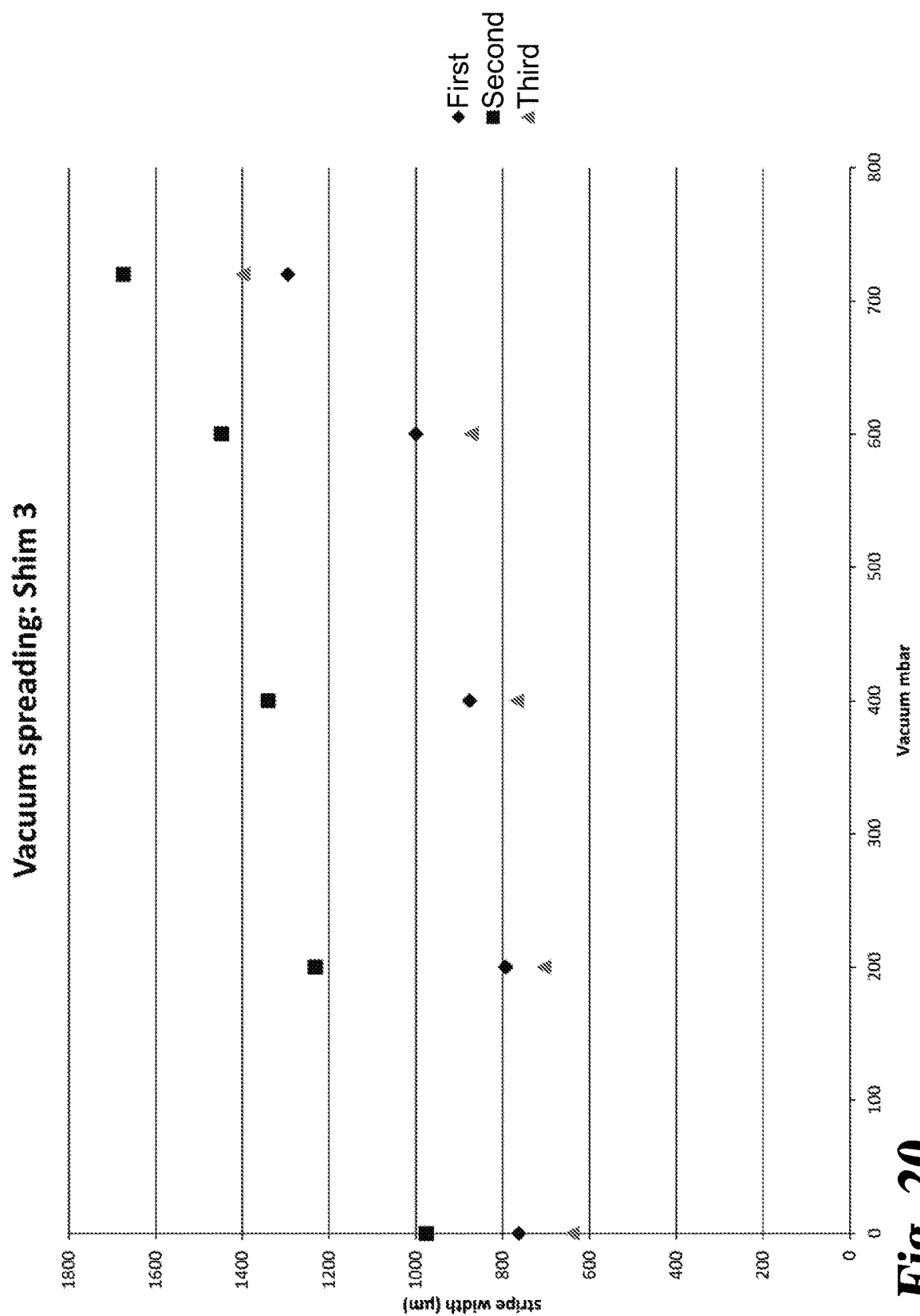
FIG. 20 is a graph of the actual spreading of a first wet film, a second wet film, and a third wet film applied to a substrate upon application of a vacuum with the use of a third slot die shim.

In Example C, the actual spreading of the wet films upon application of a vacuum is measured and displayed graphically in FIG. 20. In Example C, the slot die shim used in the testing had a width W1 of the first channel 120 of 825 µm, the width W2 of the second channel 122 was 1550 µm, and the width W3 of the third channel 124 was 810 µm of the slot die shim. The width W4 of the first divider wall 126 was 169 µm and the width W5 of the second divider wall 128 was 167 µm. In the table labeled "Actual Spreading", the widths of the first, second, and third wet films and the widths of the first and second gaps were measured under an increasing vacuum force. As the vacuum increased from 0 Pa to about 200 Pa the widths W11, W12, and W13 of the first, second, and third wet films were all less than the widths of their respective channels 120, 122, and 124. At a vacuum of 400 Pa the width W11 of the first wet film was greater than the width W1 of the first channel 120, the width W12 of the second film was less than the width W2 of the second channel 122, and the width W13 of the third film was less than the width W3 of the third channel 124. At a vacuum from about 600 Pa to 720 Pa, the widths W11, W12, and W13 of the first, second, and third wet films, were greater than the widths W1, W2, and W3 of the respective channels 120, 122, and 124. At a vacuum between 0 Pa and 600 Pa, the width W14 of the first gap and the width W15 of the second gap were larger than the width W4 of the first divider wall 126 and the width W5 of the second divider wall 128, respectively. As the vacuum increased from 600 to 720 Pa, the width W14 of the first gap and the width W15 of the second gap were each smaller than the width W4 of the first divider wall 126 and the width W5 of the second divider wall 128, respectively.

| Actual Spreading | | | | | |
| --- | --- | --- | --- | --- | --- |
| Vacuum (Pa) | 0 | 200 | 400 | 600 | 720 |
| Width W1 of First Wet Film (µm) | 763 | 793 | 877 | 1000 | 1295 |
| Width W2 of Second Wet Film (µm) | 976 | 1232 | 1340 | 1449 | 1675 |
| Width W3 of Third Wet Film (µm) | 640 | 705 | 767 | 872 | 1398 |
| Width W4 of First Gap (µm) | 521 | 410 | 335 | 256 | 119 |
| Width W5 of Second Gap (µm) | 510 | 387 | 314 | 233 | 114 |

Figure 21:
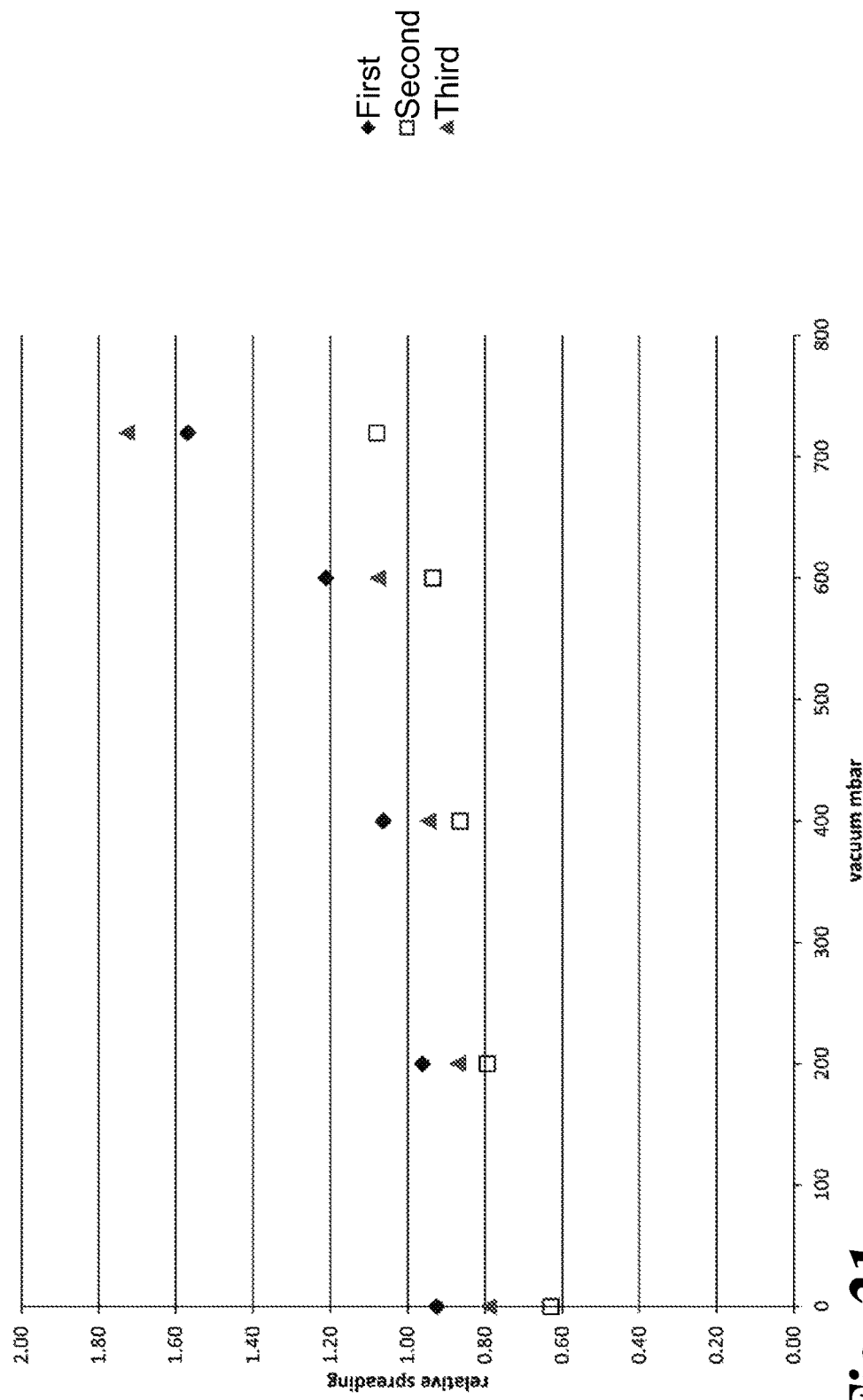
FIG. 21 is a graph of ratios of the width of wet film to the corresponding width of the channel floor at each vacuum pressure from FIG. 20.

The table "Relative Spreading" includes the ratio of the width of wet film to the corresponding width of the channel is determined at each vacuum pressure to determine the relative spreading of the wet film upon application of the vacuum. The results are displayed graphically in FIG. 21.

| Relative Spreading | | | | | |
| --- | --- | --- | --- | --- | --- |
| Vacuum (Pa) | 0 | 200 | 400 | 600 | 720 |
| First Channel | 0.92 | 0.96 | 1.06 | 1.21 | 1.57 |
| Second Channel | 0.63 | 0.79 | 0.86 | 0.93 | 1.08 |
| Third Channel | 0.79 | 0.87 | 0.95 | 1.08 | 1.73 |

As indicated above, these Examples are not to be construed as limiting the invention disclosed in this document. Moreover, it should also be appreciated that one or more of the values disclosed in these Examples may change as various process parameters, such as web speed, reagent flow rates, and vacuum change.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. A slot die apparatus, comprising:
a first die section comprising a first reservoir for a first coating and a second reservoir for a second coating;
a second die section attached to and forming a slot with the first die section;
a slot die shim received in the slot between the first and second die sections, the slot die shim including a top face having first and second channels formed in the top face and a first divider wall positioned between the first channel and the second channel,
the first channel including a first floor and a first side wall opposing the divider wall, the first channel being in communication with the first reservoir and configured to receive the first coating,
the second channel including a second floor and a second side wall opposing the divider wall on a side opposite the first wall, the second channel being in communication with the second reservoir and configured to receive the second coating,
the first channel having a first discharge opening at a discharge end of the slot die apparatus, the second channel having a separate, second discharge opening at the discharge end of the slot die apparatus, and the divider wall extending to the first and second discharge openings,
the slot die shim configured to simultaneously dispense the first coating through the first channel and the second coating through the second channel onto a substrate.

2. The apparatus of claim 1, wherein the divider wall has a thickness of between about 0.1 millimeters and about 0.5 millimeters.

3. The apparatus of claim 1, wherein the first channel has a channel depth of between about 0.1 millimeters and about 0.2 millimeters.

4. The apparatus of claim 1, wherein the first channel and the second channel each have a channel width, the channel width of the first channel being smaller than the channel width of the second channel.

5. The apparatus of claim 1, wherein the first channel and the second channel each have a dispensing edge, the dispensing edges being arranged in a parallel orientation.

6. The apparatus of claim 1, wherein the first die section comprises a third reservoir for a third coating, the top face of the slot die shim having a third channel formed in the top face and a second divider wall positioned between the second and third channels, the third channel including a third floor and a third pair of side walls wall opposing the second divider wall, the third channel having a separate, third discharge opening at the discharge end of the slot die apparatus, the second divider wall extending to the second and third discharge openings, the third channel being in communication with the third reservoir and configured to receive the third coating, the slot die shim being configured to simultaneously dispense the first, second and third coatings through the first, second and third channels, respectively, to provide the first coating, the second coating, and the third coating arranged in parallel on the substrate.

7. The apparatus of claim 1, wherein the first coating includes a first reagent for producing a first electrochemical signal in the presence of a first test analyte, and the second coating includes a second reagent for producing a second electrochemical signal in the presence of a second test analyte.

8. The apparatus of claim 7, wherein the first test analyte is glucose and the second test analyte is ketone.

9. A slot die apparatus, comprising:
- a first die section comprising a first reservoir for a first coating and a second reservoir for a second coating;
- a second die section attached to and forming a slot with the first die section;
- a slot die shim received in the slot between the first and second die sections, the slot die shim including a top face,
- the slot die shim having a first channel in communication with the first reservoir and configured to receive the first coating,
- the slot die shim having a second channel in communication with the second reservoir and configured to receive the second coating,
- the first channel comprising an open channel formed in the top face of the slot die shim facing one of the first and second die sections and forming therewith a first enclosed passageway communicating with the first reservoir and having a first opening at a discharge end of the slot die apparatus, the and second channel comprising an open channel formed in the top face of the slot die shim facing the one of the first and second die sections and forming therewith a second enclosed passageway communicating with the first and second reservoir and having a second opening at the discharge end of the slot die apparatus,
- the first and second openings being separated by a divider wall, and
- the slot die shim configured to simultaneously dispense onto a substrate the first coating through the first discharge opening and the second coating through the second discharge opening.

* * * * *